(12) United States Patent
McCarron et al.

(10) Patent No.: US 10,393,704 B2
(45) Date of Patent: Aug. 27, 2019

(54) MULTI-FREQUENCY BAW MIXING AND SENSING SYSTEM AND METHOD

(71) Applicant: Qorvo US, Inc., Greensboro, NC (US)

(72) Inventors: Kevin McCarron, Bend, OR (US); Rio Rivas, Bend, OR (US)

(73) Assignee: QORVO US, INC., Greensboro, NC (US)

( * ) Notice: Subject to any disclaimer, the term of this patent is extended or adjusted under 35 U.S.C. 154(b) by 189 days.

(21) Appl. No.: 15/339,022

(22) Filed: Oct. 31, 2016

(65) Prior Publication Data

US 2017/0122911 A1      May 4, 2017

Related U.S. Application Data

(60) Provisional application No. 62/248,397, filed on Oct. 30, 2015.

(51) Int. Cl.
  *G01N 29/036* (2006.01)
  *G01N 29/02* (2006.01)
  (Continued)

(52) U.S. Cl.
  CPC ......... *G01N 29/022* (2013.01); *G01N 29/036* (2013.01); *G01N 29/222* (2013.01); *G01N 2291/014* (2013.01); *G01N 2291/0255* (2013.01); *G01N 2291/0256* (2013.01); *G01N 2291/0426* (2013.01); *H03H 9/175* (2013.01)

(58) Field of Classification Search
  None
  See application file for complete search history.

(56) References Cited

U.S. PATENT DOCUMENTS

| 4,640,756 A | 2/1987 | Wang et al. |
| 6,320,295 B1 | 11/2001 | McGill et al. |

(Continued)

FOREIGN PATENT DOCUMENTS

| DE | 10 2006 004 448 B3 | 10/2007 |
| WO | WO 2006/063437 A1 | 6/2006 |

(Continued)

OTHER PUBLICATIONS

U.S. Appl. No. 15/339,062, filed Oct. 31, 2016.
(Continued)

*Primary Examiner* — Paul S Hyun
(74) *Attorney, Agent, or Firm* — Mueting, Raash & Gebhardt, P.A.

(57) ABSTRACT

A sensing system utilizes a channel, a BAW resonator structure including piezoelectric material with a c-axis having an inclined orientation, at least one functionalization material arranged over an active region of the BAW resonator structure, and a driving circuit configured to apply AC signals at different frequencies to cause the piezoelectric material to selectively exhibit a dominant shear response or a dominant longitudinal response. Driving the piezoelectric material in longitudinal mode induces localized fluid mixing proximate to the active region, whereas driving in shear mode permits detection of analyte bound to the at least one functionalization material in a liquid environment. Recesses may be defined in a surface of a top side electrode to enhance longitudinal mode mixing.

20 Claims, 11 Drawing Sheets

(51) Int. Cl.
*G01N 29/22* (2006.01)
*H03H 9/17* (2006.01)

(56) References Cited

U.S. PATENT DOCUMENTS

| | | | |
|---|---|---|---|
| 7,468,608 | B2 | 12/2008 | Feucht et al. |
| 8,409,875 | B2 | 4/2013 | Johal et al. |
| 9,096,823 | B1 | 8/2015 | Branch et al. |
| 2006/0054941 | A1 | 3/2006 | Lu et al. |
| 2006/0125489 | A1* | 6/2006 | Feucht ............... G01N 29/022 324/633 |
| 2006/0222568 | A1 | 10/2006 | Wang et al. |
| 2007/0210349 | A1 | 9/2007 | Lu et al. |
| 2010/0088039 | A1* | 4/2010 | Yang .................... C07K 1/20 702/23 |
| 2015/0293060 | A1 | 10/2015 | Jacobsen |
| 2017/0120242 | A1 | 5/2017 | Rivas et al. |
| 2017/0122936 | A1 | 5/2017 | Rivas et al. |
| 2017/0134002 | A1 | 5/2017 | Rivas et al. |

FOREIGN PATENT DOCUMENTS

| | | |
|---|---|---|
| WO | WO 2007/123539 A1 | 11/2007 |
| WO | PCT/US2016/059312 | 10/2016 |
| WO | PCT/US2016/059327 | 10/2016 |
| WO | PCT/US2016/059677 | 10/2016 |
| WO | WO 2017/075344 A1 | 5/2017 |
| WO | WO 2017/075354 A1 | 5/2017 |
| WO | WO 2017/083131 A1 | 5/2017 |

OTHER PUBLICATIONS

Qorvo US, Inc., "Summary of Sales Activity of Predecessor to Applicant Concerning Tilted C-Axis Aluminum Nitride Products," Unpublished, Jan. 10, 2017, 1 page.
Bjurström, J. et al., "Design and Fabrication of Temperature Compensated Liquid FBAR Sensors," IEEE Ultrasonics Symposium, Oct. 2-6, 2006, pp. 894-897.
Chen, Qingming et al., "Characteristics of Dual Mode AlN Thin Film Bulk Acoustic Wave Resonators," 2008 IEEE International Frequency Control Symposium, May 19-21, 2008, IEEE, pp. 609-614.
Chen, Ying-Chung et al., "The Liquid Sensor Using Thin Film Bulk Acoustic Resonator with C-Axis Tilted AlN Films," Journal of Nanomaterials, vol. 2013, Article ID 245095, 2013, 8 pages.
Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.
Fan, Xiao Zhu et al., "An adaptive feedback circuit for MEMS resonators," Journal of Micromechanics and Microengineering, vol. 21, Mar. 1, 2011, 10 pages.
Groner, M. D. et al., "Gas diffusion barriers on polymers using $Al_2O_3$ atomic layer deposition," Applied Physics Letters, vol. 88, Jan. 31, 2006, pp. 051907-1 to 051907-3.
Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.
Luo, J. K. et al., "Acoustic Wave Based Microfluidics and Lab-on-a-Chip," Modeling and Measurement Methods for Acoustic Waves and for Acoustic Microdevices, Chapter 21, Aug. 28, 2013, InTech, pp. 515-556.
Meyer, Jens et al., "$Al_2O_3$/$ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.
Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.
Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.
Nguyen, Nam-Trung et al., "Micromixers—a review," Journal of Micromechanics and Microengineering, vol. 15, Dec. 8, 2004, pp. R1-R16.
Nirschl, Martin et al., "CMOS-Integrated Film Bulk Acoustic Resonators for Label-Free Biosensing," Sensors, vol. 10, No. 5, Apr. 27, 2010, pp. 4180-4193.
Qin, Lifeng et al., "Analytical Study of Dual-Mode Thin Film Bulk Acoustic Resonators (FBARs) Based on ZnO and AlN Films With Tilted c-Axis Orientation," IEEE Transactions on Ultrasonics, Ferroelectrics, and Frequency Control, vol. 57, No. 8, Aug. 2010, pp. 1840-1853.
Stroock, Abraham D. et al., "Chaotic Mixer for Microchannels," Science, vol. 295, Jan. 25, 2002, pp. 647-651.
Suh, Yong Kweon et al., "A Review on Mixing in Microfluidics," Micromachines, vol. 1, No. 3, Sep. 30, 2010, pp. 82-111.
Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.
U.S. Appl. No. 15/293,063, filed Oct. 13, 2016, McCarron et al.
Author unknown, "Acoustic Wave Sensors," Vectron International, Date Unknown, 44 pages, <www.sengenuity.com/tech_ref/AWS_WebVersion.pdf>.
Miller, "The Stokes-Einstein Law for Diffusion in Solution," *Proceedings of the Royal Society of London. Series A, Containing Papers of a Mathematical and Physical Character* (1905-1934), Jan. 1924, 106(70):724-49.
Rabus et al., "A high sensitivity open loop electronics for gravimetric acoustic wave-based sensors," Jun. 2013, *IEEE Transactions on Ultrasonics, Ferroelectrics, and Frequency Control*, 60(6):1219-1226.
Ramakrishnan, et al., "Resonant Frequency Characteristics of a SAW Device Attached to Resonating Micropiliars," 2012, *Sensors*, 12(4):3789-97.
Zhang et al., "A Microfluidic Love-Wave Biosensing Device for PSA Detection Based on an Aptamer Beacon Probe," 2015, *Sensors*, 15:13839-850.
Zhou, et al., "Interfacial Structures and Properties of Organic Materials for Biosensors: An Overview," *Sensors*, Nov. 6, 2012, 12:15036-062.
U.S. Appl. No. 62/247,233, filed Oct. 28, 2015, Rivas.
U.S. Appl. No. 62/248,392, filed Oct. 30, 2015, Rivas.
U.S. Appl. No. 62/252,688, filed Nov. 9, 2015, Rivas.
U.S. Appl. No. 15/337,338, filed Oct. 28, 2016, Rivas et al.
U.S. Appl. No. 15/337,429, filed Oct. 28, 2016, Rivas et al.
U.S. Appl. No. 15/339,062, filed Oct. 31, 2016, Rivas et al.
International Patent Application No. PCT/US2016/059312, filed Oct. 28, 2016; International Search Report / Written Opinion dated Feb. 13, 2017; 12 pages.
International Patent Application No. PCT/US2016/059312, filed Oct. 28, 2016; International Preliminary Report on Patentability dated May 11, 2018; 8 pages.
International Patent Application No. PCT/US2016/059327, filed Oct. 28, 2016; International Search Report / Written Opinion dated Feb. 13, 2017; 15 pages.
International Patent Application No. PCT/US2016/059327, filed Oct. 28, 2016; International Preliminary Report on Patentability dated May 11, 2018; 9 pages.
International Patent Application No. PCT/US2016/059677, filed Oct. 31, 2016; International Search Report / Written Opinion dated May 18, 2017; 11 pages.
International Patent Application No. PCT/US2016/059677, filed Oct. 31, 2016; International Preliminary Report on Patentability dated May 24, 2018; 9 pages.
Chapter 21. Lou et al., "Acoustic Wave Based Microfluidics and Lab-on-a-Chip," in *Modeling and Measurement Methods for Acoustic Waves and for Acoustic Microdevices*. InTech: Aug. 28, 2013. 515-56.
Fu et al., "Aluminium Nitride thin Film Acoustic Wave Device for Microfluidic and Biosensing Applications," Sep. 1, 2010, *Acoustic*

(56) References Cited

OTHER PUBLICATIONS

*Waves*, retrieved on Nov. 14, 2016 from the Internet. Retrieved from the Internet: <URL:https://www/researchgate/net/profile/MPY_Desmulliez/publication/267951195_Aluminium_Nitride_thin_Film-Acoustin_Wave_Device_for_Microfluidic_and_Biosensing_Applications/links/5450dd8b0cf295b561637e62.pdf>; 263-98pgs.

Katardjiev et al., "Recent developments in thin film electro-acoustic technology for biosensor applications," Oct. 19, 2011, *Vacuum*, 86(5):520-31.

"The Laser MicroJet® Technology: A Simple Principle," Synova: Cool Last Micro-Machining, Feb. 17, 2015; 8 pages.

Lee et al., "Microfluidic Mixing: A Review," May 18, 2011, *International Journal of Molecular Sciences*, 12:3263-87.

Montagut, Yeison et al. "QCM Technology in Biosensors," Biosensors—Emerging Materials and Applications, Chapter 9, 2011, INTECH Open Access Publisher, pp. 153-178.

Through Silicon Vias (TSV) for backside electrical connection are common in devices https://en.wikipedia.org/wiki/Through-silicon_via.

Voiculescu, et al., "Acoustic wave based MEMS devices for biosensing applications", 2012, *Biosensors and Bioelectronics*, 33:1-9. Published online Jan. 16, 2012.

Wingqvist, et al., "Shear mode AlN thin film electro-acoustic resonant sensor operation in viscous media", 2007, *Sensors and Actuators B*, 123:466-473. Published online Nov. 2, 2006.

Zhang, et al., "A single-chip biosensing platform integrating FBAR sensor with digital microfluidic device", *2014 IEEE International Ultrasonics Symposium Proceedings*, 2014, 3 pages.

\* cited by examiner

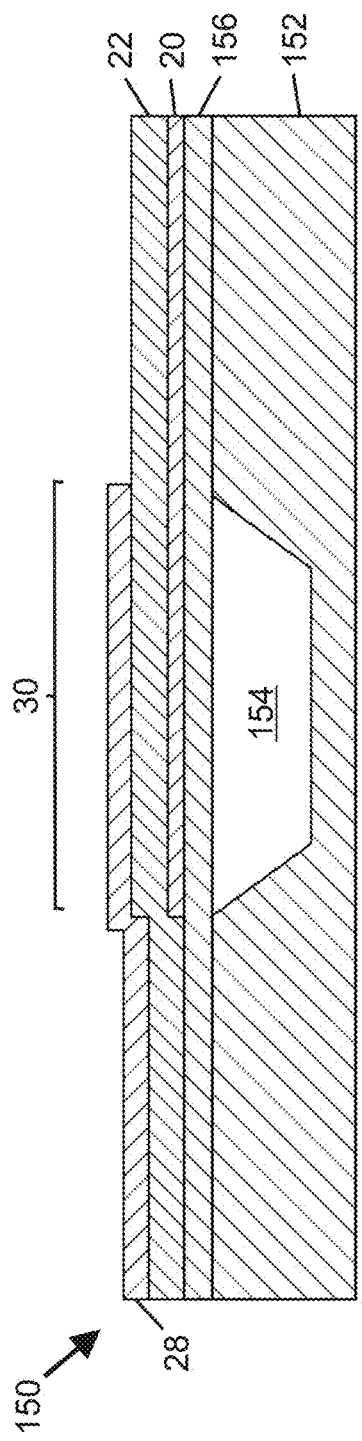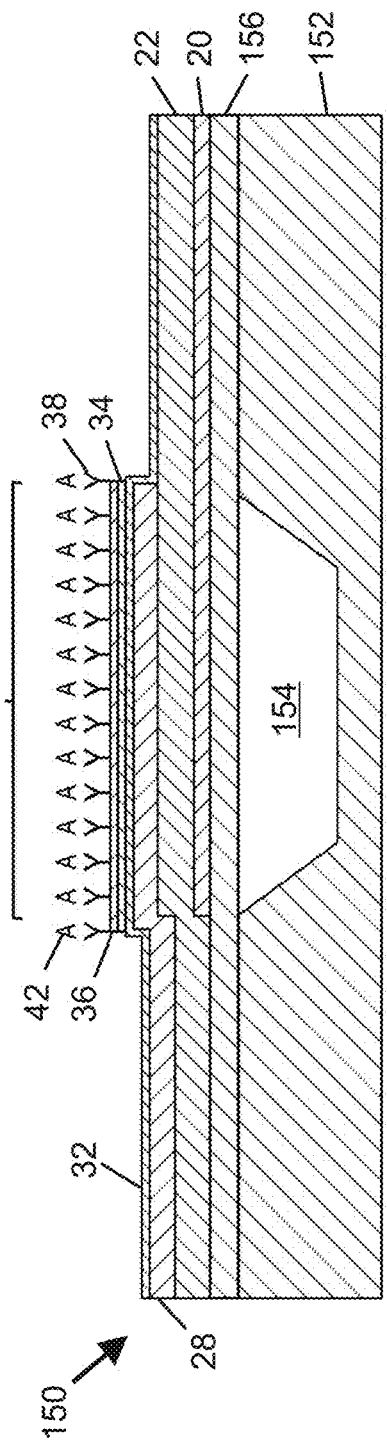
FIG. 11A
FIG. 11B

US 10,393,704 B2

MULTI-FREQUENCY BAW MIXING AND SENSING SYSTEM AND METHOD

STATEMENT OF RELATED APPLICATIONS

This application claims the benefit of provisional patent application Ser. No. 62/248,397, filed Oct. 30, 2015, the disclosure of which is hereby incorporated herein by reference in its entirety. Subject matter disclosed herein also relates to U.S. patent application Ser. No. 15/339,062 entitled "BAW Sensor with Enhanced Surface Area Active Region" filed on Oct. 31, 2016, the contents of which are hereby incorporated by reference as if set forth fully herein.

TECHNICAL FIELD

The present disclosure relates to fluidic devices incorporating acoustic resonators, including fluidic devices and related systems suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample. The term "functionalization material" may be used herein to generally relate to both specific and non-specific binding materials. Transduction methods used with biosensors may be based on various principles, such as electrochemical, optical, electrical, acoustic, etc. Among these, acoustic transduction offers a number of potential advantages, such as being real time, label-free, and low cost, as well as exhibiting high sensitivity.

An acoustic wave device employs an acoustic wave that propagates through or on the surface of a specific binding material, whereby any changes to the characteristics of the propagation path affect the velocity and/or amplitude of the wave. Acoustic wave devices are commonly fabricated by micro-electromechanical systems (MEMS) fabrication techniques, owing to the need to provide microscale features suitable for facilitating high-frequency operation. Presence of functionalization material on or over an active region of an acoustic wave device permits an analyte to be bound to the functionalization material, thereby altering the mass being vibrated by the acoustic wave and altering the wave propagation characteristics (e.g., velocity, thereby altering resonance frequency). Changes in velocity can be monitored by measuring the frequency, magnitude, and/or phase characteristics of the acoustic wave device and can be correlated to a physical quantity being measured.

In the case of a piezoelectric crystal resonator, an acoustic wave may embody a bulk acoustic wave (BAW) propagating through the interior (or "bulk") of a piezoelectric material. BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids because shear waves do not impart significant energy into fluids.

Certain piezoelectric thin films are capable of exciting both longitudinal and shear mode resonance, such as hexagonal crystal structure piezoelectric materials including aluminum nitride (AlN) and zinc oxide (ZnO). To excite a wave including a shear mode using a standard sandwiched electrode configuration device, a polarization axis in a piezoelectric thin film must generally be non-perpendicular to (e.g., tilted relative to) the film plane. In biological sensing applications involving a liquid media, the shear component of a resonator is used because it is not damped completely by liquid loading. In this case, the piezoelectric material is grown with a c-axis orientation distribution that is non-perpendicular relative to a face of an underlying substrate to enable a bulk acoustic wave resonator structure to exhibit a dominant shear response upon application of an alternating current across electrodes thereof.

An electromechanical coupling coefficient is a numerical value that represents the efficiency of piezoelectric materials in converting electrical energy into acoustic energy for a given acoustic mode. Changing the c-axis angle of inclination for hexagonal crystal structure piezoelectric materials causes variation in shear and longitudinal coupling coefficients. FIG. 1 embodies a plot of shear coupling coefficient ($K_s$) and longitudinal coupling coefficient ($K_l$) each as a function of c-axis angle of inclination for AlN, although other piezoelectric materials show similar behavior. At certain angles (e.g., 46° and 90°) the longitudinal component is minimized and $K_l$ has a zero value, and at certain angles (e.g., 0° and 67°) the shear component is minimized and $K_s$ has a zero value. At all other angles of C-axis inclination, there exist both shear and longitudinal components of wave propagation. Devices built with C-axis angles that include both longitudinal and shear modes (e.g., at angles except for about 0°, 46°, 67°, and 90°) are referred to as quasi-shear mode devices. Quasi-shear mode acoustic resonator devices may be incorporated in fluidic devices providing sensing utility.

Under typical operating conditions, flows in microfluidic channels (also termed "microchannels") are laminar. Fluids in laminar flow tend to follow parallel streamline paths, such that the chaotic fluctuations of velocity that tend to homogenize fluids in turbulent flows are absent. Multiple fluids introduced in a standard microchannel generally will not mix with each other, except at a common interface between the fluids via diffusion, and the diffusion process is typically slow compared with the flow of fluid along a principal axis of a microfluidic channel. The same principles that inhibit rapid mixing of fluids flowing under laminar conditions in a microfluidic channel also affect the distribution of analytes contained in one or more fluids flowing within a microfluidic channel. Fick's first law of diffusion states that flux moves from regions of high concentration to regions of low concentration. Secondarily, the flux rate is proportional to the concentration gradient difference. In a volume of fluid containing an analyte and advancing in a horizontal direction through a microfluidic channel having functionalization material arranged along a bottom surface of the channel, the fluid volume may be modeled as a moving "stack" of horizontal fluid layers. Even if it is assumed that analyte concentration is constant in each layer of the stack forming the fluid volume upon entering the microfluidic channel, following passage of the fluid volume over the functionalization material, a lowermost fluid layer of the stack will exhibit reduced or depleted analyte concentration due to binding of analyte with the functionalization material. But since diffusion is slow in a direction perpendicular to the direction of fluid flow through the microfluidic channel, and analyte needs to diffuse to a surface bearing functionalization material to bind, analyte present in fluid layers other than the lowermost fluid layer may not be available for binding with the functionalization material along the bottom surface of the channel within a reasonable period of time. Therefore, analyte concentration may remain stratified within the channel until diffusion occurs. Additionally, large analyte molecules may require a long time to bind with functionalization material.

Thus, conventional biochemical sensing devices may suffer from inconsistent distribution of target species in a sample and/or a low rate of analyte binding that may extend the time necessary to complete measurement of a particular sample. Accordingly, there is a need for fluidic devices incorporating BAW resonator structures, such as for biosensing or biochemical sensing applications, that overcome limitations associated with conventional devices.

SUMMARY

The present disclosure provides a sensing system that utilizes a channel arranged to receive a fluid, a bulk acoustic wave (BAW) resonator structure including a piezoelectric material comprising a c-axis having an orientation distribution that is predominantly non-parallel to normal of a face of a substrate, at least one functionalization material arranged over a top side electrode of the BAW resonator structure and arranged to contact fluid received by the channel, and a driving circuit that is configured to apply alternating current at different frequencies to cause the piezoelectric material to selectively exhibit a dominant shear response or a dominant longitudinal response. Sensing methods are also provided. The at least one functionalization material is preferably configured to bind at least one analyte contained in the fluid. Driving of the BAW resonator structure at a frequency configured to cause the piezoelectric material to exhibit a dominant longitudinal response tends to promote mixing of analyte in the fluid, thereby increase a rate of binding of analyte to the at least one functionalization material. Driving of the BAW resonator at another frequency configured to cause the piezoelectric material to exhibit a dominant shear response is useful to permit detection of analyte bound to the at least one functionalization material, whereby a change in electroacoustic response (e.g., at least one of amplitude magnitude property, a frequency property, or a phase property) of the BAW resonator structure during dominant shear mode vibration may be detected to indicate a presence and/or quantity of analyte bound to the at least one functionalization material. A top side electrode of a bulk acoustic wave resonator structure may include at least one recess that is defined in a surface of the top side electrode proximate to a fluidic channel, wherein the at least one recess may induce rotary movement (and localized mixing) of fluid proximate to the at least one recess upon application of an alternating current signal configured to cause the bulk acoustic wave resonator structure incorporating the top side electrode to exhibit a dominant longitudinal response. Enhancement of mixing of analyte in a fluid sample proximate to functionalization material overlying an active region of a BAW resonator structure may increase a rate of binding of analyte to the functionalization material, thereby reducing the time necessary to complete measurement of a particular sample.

In one aspect, a sensing system includes: a channel arranged to receive a fluid; a bulk acoustic wave resonator structure arranged between a substrate and a surface bounding at least a portion of the channel, wherein the bulk acoustic wave resonator structure includes (i) a piezoelectric material comprising a c-axis having an orientation distribution that is predominantly non-parallel to normal of a face of the substrate, (ii) a bottom side electrode arranged between the piezoelectric material and the substrate, and (iii) a top side electrode arranged between the piezoelectric material and the channel, wherein at least a portion of the piezoelectric material is arranged between the bottom side electrode and the top side electrode to form an active region; at least one functionalization material arranged over at least a portion of the top side electrode, wherein the at least one functionalization material is arranged to contact the fluid received by the channel; and a driving circuit configured to apply alternating current across the bottom side electrode and the top side electrode at a first frequency configured to cause the piezoelectric material to exhibit a dominant shear response, and configured to apply alternating current across the bottom side electrode and the top side electrode at a second frequency configured to cause the piezoelectric material to exhibit a dominant longitudinal response.

In certain embodiments, the sensing system further includes a detection circuit configured to detect a change in electroacoustic response of the bulk acoustic wave resonator structure upon interaction of an analyte contained in the fluid and the at least one functionalization material. For example, when analyte is bound to functionalization material overlying an active region of a bulk acoustic wave (BAW) resonator structure, the increased mass loaded on the active region generally causes a resonant frequency of the BAW resonator structure to decline, such that detection of the altered resonant frequency provides an indication of the presence and/or amount of analyte adsorbed by the functionalization material.

In certain embodiments, the top side electrode comprises at least one recess that is defined in a surface of the top side electrode proximate to the channel. In certain embodiments, the top side electrode comprises at least one lateral edge, and the at least one recess includes terminal ends non-coincident with the at least one lateral edge. In certain embodiments, the at least one recess comprises a first recess and a second recess, wherein the second recess is laterally displaced and non-intersecting relative to the first recess. In certain embodiments, the at least one recess comprises a plurality of substantially parallel recesses. In certain embodiments, the at least one recess comprises a plurality of substantially concentric recesses, and each recess of the plurality of substantially concentric recesses is shaped as a major arc.

In certain embodiments, the at least one functionalization material comprises at least one of a specific binding material or a non-specific binding material.

In certain embodiments, the sensing system further includes a self-assembled monolayer arranged between the top side electrode and the at least one functionalization material.

In certain embodiments, the sensing system further includes an interface layer arranged between the top side electrode and the at least one functionalization material. In certain embodiments, the top side electrode comprises a non-noble metal, and the bulk acoustic wave resonator structure further comprises a hermeticity layer arranged between the interface layer and the top side electrode. In certain embodiments, the sensing system further includes a self-assembled monolayer arranged between the interface layer and the at least one functionalization material.

In certain embodiments, the sensing system further includes at least one acoustic reflector element arranged between the substrate and the bulk acoustic wave resonator structure.

In certain embodiments, the substrate defines a recess, and the active region is arranged over at least a portion of the recess. In certain embodiments, a support layer is provided between the bulk acoustic wave resonator structure and the recess, wherein the active region is arranged over at least a portion of the support layer and at least a portion of the recess.

In certain embodiments, the channel comprises at least one dimension of less than about 500 microns.

In another aspect, a method for biological or chemical sensing comprises: supplying a fluid containing an analyte into a channel of a sensing system as disclosed herein, wherein said supplying is configured to cause at least some of the analyte to bind to the at least one functionalization material; inducing a bulk acoustic wave in the active region; and detecting a change in electroacoustic response in at least one of a frequency property or a phase property of the bulk acoustic wave resonator structure upon binding of analyte to the at least one functionalization material.

In another aspect, a sensing method includes: supplying a fluid containing an analyte to a channel arranged proximate to a bulk acoustic wave resonator structure comprising a piezoelectric material including a c-axis having an orientation distribution that is predominantly non-parallel to normal of a face of a substrate, wherein at least a portion of the piezoelectric material is arranged between a top side electrode and a bottom side electrode to form an active region, at least one functionalization material is arranged over at least a portion of the active region, and the at least one functionalization material is arranged to contact the fluid supplied to the channel; driving the bulk acoustic wave resonator structure at a first frequency configured to cause the piezoelectric material to exhibit a dominant longitudinal response to increase a rate of binding of analyte in the fluid to the at least one functionalization material; driving the bulk acoustic wave resonator structure at a second frequency configured to cause the piezoelectric material to exhibit a dominant shear response; and while driving the bulk acoustic wave resonator structure at the second frequency, detecting a change in electroacoustic response of the at least one bulk acoustic wave resonator structure caused by binding of analyte to the at least one functionalization material.

In certain embodiments, said driving of the bulk acoustic wave resonator structure at the first frequency is performed during a first time window, and said driving of the bulk acoustic wave resonator structure at the second frequency is performed during a second time window, wherein the second time window is non-overlapping with the first time window.

In certain embodiments, said driving of the bulk acoustic wave resonator structure at the first frequency is performed during a first time window, and said driving of the bulk acoustic wave resonator structure at the second frequency is performed during a second time window, wherein at least a portion of the second time window overlaps the first time window.

In certain embodiments, the top side electrode comprises at least one recess that is defined in a surface of the top side electrode proximate to the channel, and said driving of the bulk acoustic wave resonator structure at the first frequency is configured to induce localized rotational motion of the fluid proximate to the at least one recess.

In another aspect, a fluidic device includes: a channel arranged to receive a fluid; and a bulk acoustic wave resonator structure arranged between a substrate and a surface bounding at least a portion of the channel, wherein the bulk acoustic wave resonator structure includes (i) a piezoelectric material comprising a c-axis having an orientation distribution that is predominantly non-parallel to normal of a face of the substrate, (ii) a bottom side electrode arranged between the piezoelectric material and the substrate, and (iii) a top side electrode arranged between the piezoelectric material and the channel, wherein at least a portion of the piezoelectric material is arranged between the bottom side electrode and the top side electrode to form an active region. The top side electrode includes at least one recess that is defined in a surface of the top side electrode proximate to the channel. The at least one channel may be provided in various configurations as disclosed herein. For example, in certain embodiments, the at least one recess comprises a first recess and a second recess, wherein the second recess is laterally displaced and non-intersecting relative to the first recess.

In certain embodiments, the fluidic device further includes at least one functionalization material arranged over at least a portion of the top side electrode, wherein the at least one functionalization material is arranged to contact the fluid received by the channel. In certain embodiments, a self-assembled monolayer, an interface layer, and/or a hermeticity layer may be provided between the at least one functionalization material and the piezoelectric material and/or top side electrode of the bulk acoustic wave resonator structure.

In another aspect, any one or more aspects or features of one or more embodiments may be combined with aspects or features of one or more other embodiments for additional advantage, unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 11A is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity covered by an optional support layer, and an active region registered with the cavity with a portion of the piezoelectric material arranged between overlapping portions of a top side electrode and a bottom side electrode.

FIG. 11B is a schematic cross-sectional view of a FBAR structure according to FIG. 11A, following addition of a hermeticity layer, an interface layer, a self-assembled monolayer, and a functionalization (e.g., specific binding) material over at least portions of the FBAR structure.

DETAILED DESCRIPTION

Figure 1:
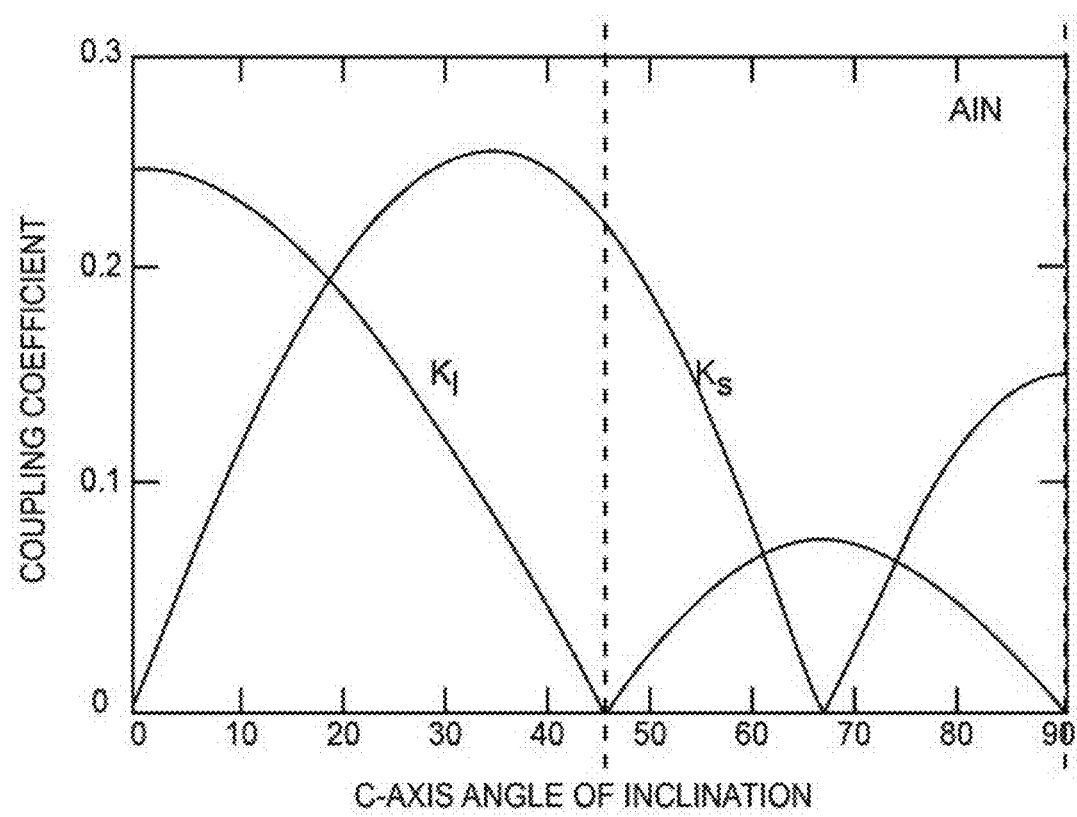
FIG. 1 is a plot of shear coupling coefficient ($K_s$) and longitudinal coupling coefficient ($K_l$) as a function of c-axis angle of inclination for AlN.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

Sensing systems disclosed herein utilize a channel arranged to receive a fluid, a bulk acoustic wave (BAW) resonator structure including a piezoelectric material comprising a c-axis having an orientation distribution that is predominantly non-parallel to normal of a face of a substrate, at least one functionalization material arranged over a top side electrode of the BAW resonator structure and arranged to contact fluid received by the channel, and a driving circuit that is configured to apply alternating current at different frequencies to cause the piezoelectric material to selectively exhibit a dominant shear response or a dominant longitudinal response. The term "dominant shear response" as used herein refers to motion with a greater shear (e.g., horizontal) magnitude than longitudinal (e.g., vertical) magnitude. Similarly, the term "dominant longitudinal response" as used herein refers to motion with a greater longitudinal (e.g., vertical) magnitude than shear (e.g., horizontal) magnitude. The at least one functionalization material is preferably configured to bind at least one analyte contained in the fluid. When the BAW resonator structure is driven at a frequency configured to cause the piezoelectric material to exhibit a dominant longitudinal response, such condition promotes mixing of analyte in the fluid and thereby increases a rate of binding of analyte to the at least one functionalization material. When the BAW resonator structure is driven at another frequency configured to cause the piezoelectric material to exhibit a dominant shear response, such condition enables detection of analyte bound to the at least one functionalization material. In particular, a change in electroacoustic response (e.g., at least one of amplitude magnitude property, a frequency property, or a phase property) of the BAW resonator structure during dominant shear mode vibration may be detected to indicate a presence and/or quantity of analyte bound to the at least one functionalization material. Thus, the same BAW resonator structure may be used for both mixing (i.e., thereby enhancing binding rate) and detection. Additionally, or alternatively, a top side electrode of a bulk acoustic wave resonator structure may include at least one recess that is defined in a surface of the top side electrode proximate to a fluidic channel, wherein the at least one recess may induce rotary movement (and localized mixing) of fluid proximate to the at least one recess upon application of an alternating current signal configured to cause the bulk acoustic wave resonator structure incorporating the top side electrode to exhibit a dominant longitudinal response. Enhancement of analyte binding rate may be particularly advantageous in situations involving low analyte concentration and/or large analyte molecules that may not bind quickly with functionalization material.

In certain embodiments, a BAW resonator structure comprises a hexagonal crystal structure piezoelectric material (e.g., aluminum nitride or zinc oxide) that includes a c-axis having an orientation distribution that is non-parallel (and also non-perpendicular) to normal of a face of a substrate over which the piezoelectric material is formed, thereby providing a quasi-shear mode acoustic resonator. Such a c-axis orientation distribution enables creation of shear displacements at certain frequencies (which beneficially enables operation of a BAW resonator-based sensing device in liquid environments), and enables creation of longitudinal displacements at other frequencies (which may be useful to promote localized mixing). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric materials having an inclined c-axis orientation are disclosed in U.S. Pat. No. 4,640,756 issued on Feb. 3, 1987, with the foregoing patent hereby being incorporated by reference herein.

Before describing schemes for applying alternating current at different frequencies to cause the piezoelectric material to selectively exhibit a dominant shear response or a dominant longitudinal response, exemplary bulk acoustic wave MEMS resonator devices, associated layers useful for providing biochemical sensing utility, and fluidic devices incorporating MEMS resonator devices will be introduced.

A preferred micro-electrical-mechanical system (MEMS) resonator device according to certain embodiments includes a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with an active region of the BAW resonator structure), such as: a hermeticity layer (e.g., to protect the top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material.

Figure 2:
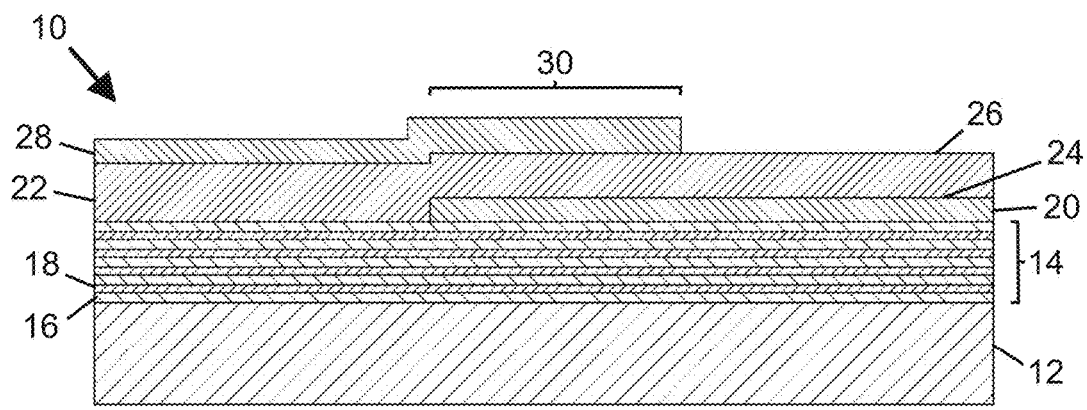
FIG. 2 is a schematic cross-sectional view of a portion of a bulk acoustic wave (BAW) MEMS resonator device usable with embodiments disclosed herein, including an active region with a piezoelectric material arranged between overlapping portions of a top side electrode and a bottom side electrode.

FIG. 2 is a schematic cross-sectional view of a portion of a bulk acoustic wave MEMS resonator device 10 useable with embodiments disclosed herein. The resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

In certain embodiments, the piezoelectric material 22 comprises a hexagonal crystal structure piezoelectric material (e.g., aluminum nitride or zinc oxide) that includes a c-axis having an orientation distribution that is predominantly non-parallel (and may also be non-perpendicular to) to normal of a face of the substrate 12. Under appropriate conditions, presence of a c-axis having an orientation distribution that is predominantly non-parallel to normal of a face of a substrate enables a BAW resonator structure to be configured to exhibit a dominant shear response upon application of an alternating current signal across a top side electrode and a bottom side electrode.

The bulk acoustic wave MEMS resonator device 10 shown in FIG. 2 lacks any layers (e.g., including functionalization material) overlying the active region 30 that would permit the resonator device 10 to be used as a biochemical sensor. If desired, at least portions of the resonator device 10 shown in FIG. 2 (e.g., including the active region 30) may be overlaid with various layers, such as one or more of: a hermeticity layer, an interface layer, a self-assembled monolayer (SAM), and/or functionalization material (which may include specific binding material or non-specific binding material).

Figure 3:
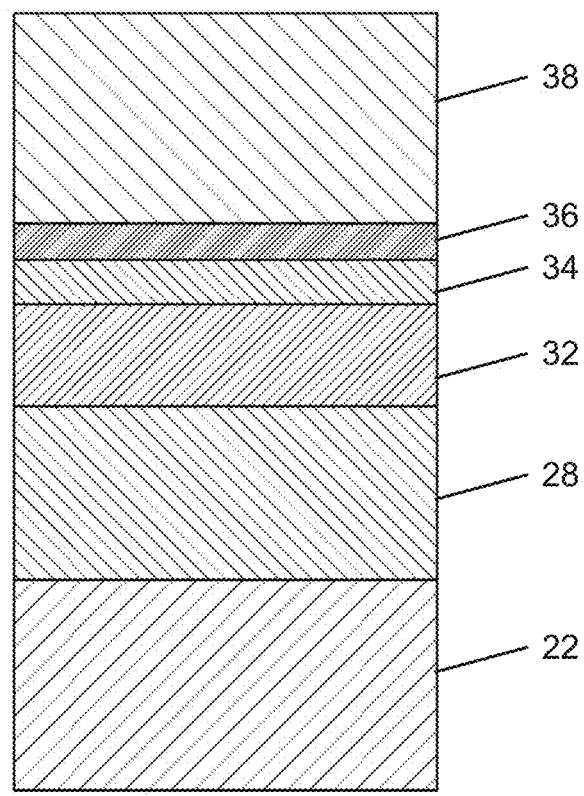
FIG. 3 is a schematic cross-sectional view of an upper portion of a BAW MEMS resonator device including a piezoelectric material and a top side electrode overlaid with a hermeticity layer, an interface layer, a self-assembled monolayer (SAM), and functionalization (e.g., specific binding) material.

FIG. 3 is a schematic cross-sectional view of an upper portion of a BAW MEMS resonator device including a piezoelectric material 22 and a top side electrode 28 overlaid with a hermeticity layer 32, an interface layer 34, a self-assembled monolayer (SAM) 36, and a functionalization (e.g., specific binding) material 38. In certain embodiments, one or more blocking materials (not shown) may be applied during fabrication, such as over portions of an interface layer to prevent localized attachment of one or more subsequently deposited layers, or (if applied over selected regions of a SAM or a functionalization material) to prevent analyte capture in regions not overlying an active region of the BAW MEMS resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide ($SiO_2$). Alternative materials incorporating hydroxylated oxide surfaces for forming interface layers include titanium dioxide ($TiO_2$), tantalum pentoxide ($Ta_2O_5$), and hafnium oxide ($HfO_2$). Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2$/day). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 g/m$^2$/day) according to certain embodiments. In certain embodiments, a hermeticity layer includes at least one of aluminum oxide ($Al_2O_3$) or silicon nitride (SiN). In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of a BAW resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a back bone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UST, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, functionalization materials may be applied on or over a SAM using a microarray spotting needle or other suitable methods. In certain embodiments, an interface layer may be patterned (e.g., using photolithography and selective etching for defining the interface layer) with a high dimensional tolerance over only a portion of a resonator structure (which includes a substrate), a SAM may be applied over the interface layer, and a subsequently applied functionalization material may be attached only to the SAM. In certain embodiments, patterning of an interface layer may provide a higher dimensional tolerance for positioning of the functionalization material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different functionalization (e.g., specific binding) materials may be provided over different active areas of a multi-resonator structure (i.e., one or more resonator structures including multiple active regions), optionally in combination with one or more active areas that are devoid of functionalization materials to serve as comparison (or "reference") regions. In certain embodiments, a functionalization material (e.g., bio-functionalization) may provide non-specific binding utility.

Certain embodiments are directed to a fluidic device including multiple bulk acoustic wave MEMS resonator structures as disclosed herein and including a fluid passage (e.g., a channel, a chamber, or the like) arranged to conduct a liquid to contact at least one functionalization (e.g., specific binding) material arranged over at least one active region of the resonator structures. Such a device may be microfluidic in scale, and may comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic channel over a first bulk acoustic wave MEMS resonator structure with an active region thereof arranged along a bottom surface of a microfluidic passage, and then enclosing the microfluidic passage using a cover or cap layer that may define fluidic ports (e.g., openings) enabling fluid communication with the microfluidic passage. In certain embodiments, functionalization (e.g., specific binding) material may be pre-applied to the active region of a bulk acoustic wave MEMS resonator structure before formation of a microfluidic channel; in other embodiments, functionalization material may be applied over an active region of a bulk acoustic wave resonator structure following formation of a microfluidic channel.

Walls of a microfluidic channel may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM layer, functionalization material, and/or blocking layers, with an SU-8 negative epoxy resist or other photoresist material. In certain embodiments, a cover or cap layer may be integrally formed with one or more walls (e.g., via molding or another suitable process) to define a portion of an upper boundary as well as lateral boundaries of at least one fluidic channel, and the integrally formed partial cover/wall structure may be applied (e.g., adhered or otherwise bonded) over at least a portion of a bulk acoustic wave resonator structure to enclose the at least one fluidic channel.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)-containing materials. An ideal blocking buffer would bind to all potential sites of non-specific interaction away from an active region. To optimize a blocking buffer for a particular analysis, empirical testing may be used to determine signal-to-noise ratio. No single chemical or biological blocking material is ideal for every situation, since each antibody-antigen pair has unique characteristics.

Figure 4:
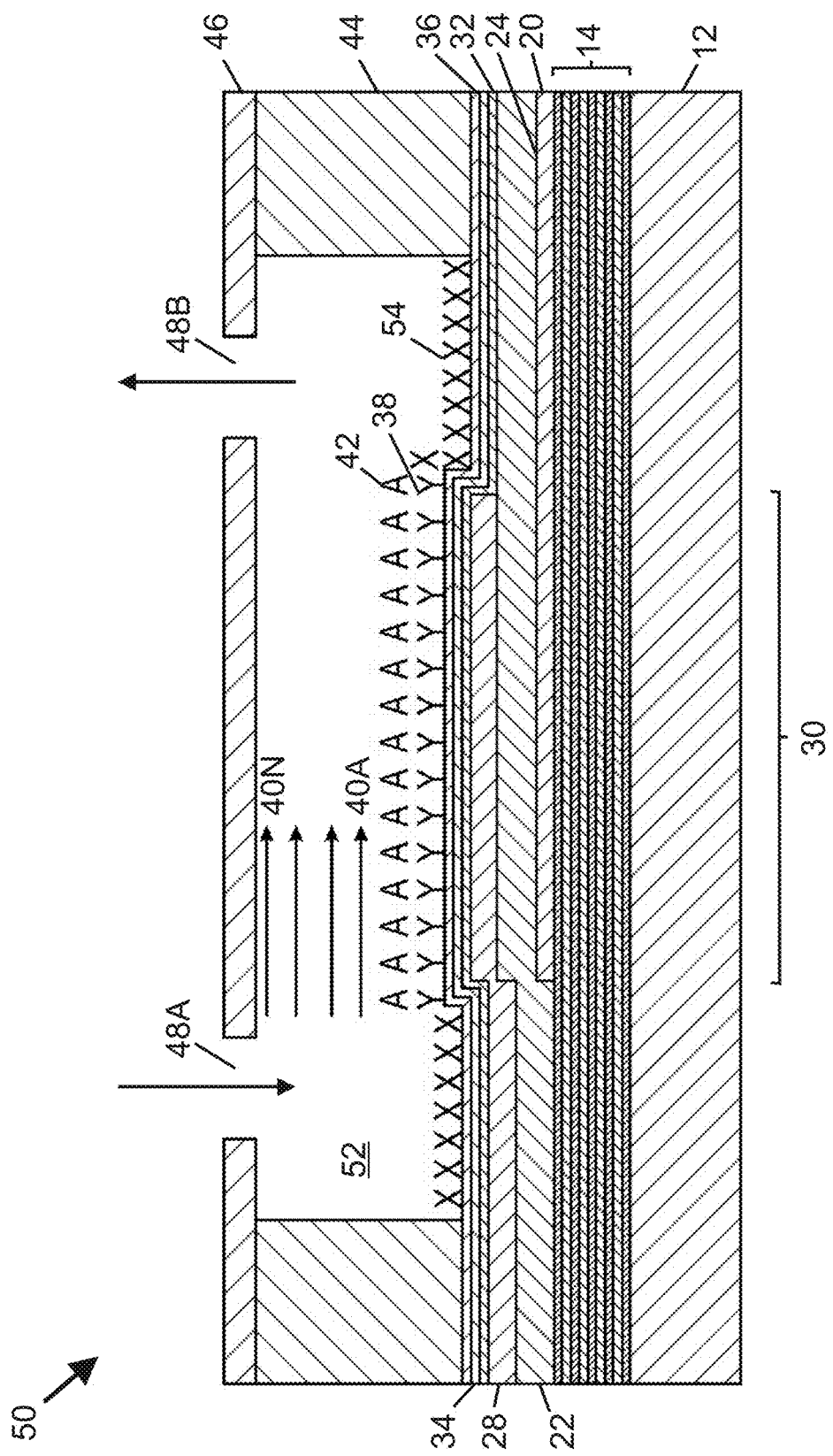
FIG. 4 is a schematic cross-sectional view of a portion of a fluidic device (e.g., a biochemical sensor device) including a microfluidic passage bounded from below by a BAW resonator structure, bounded laterally by walls, and bounded from above by a cover or cap layer defining fluidic ports, with a sequentially applied hermeticity layer, interface layer, SAM, and functionalization material covering the BAW resonator structure, according to one embodiment.

FIG. 4 is a schematic cross-sectional view of a portion of a fluidic device 50 (e.g., a biochemical sensor device) including a microfluidic passage 52 that is bounded from below by a bulk acoustic wave (BAW) MEMS resonator structure including an active region 30, bounded laterally by walls 44, and bounded from above by a cover or cap layer 46 defining fluidic ports 48A, 48B, with the fluidic device 50 being useable with various embodiments disclosed herein. The fluidic device 50 includes a substrate 12 overlaid with an acoustic reflector 14, and a bottom side electrode 20 arranged generally below a piezoelectric material 22 (i.e., along a lower surface 24 of the piezoelectric material 22). A top side electrode 28 extends over a portion of the piezoelectric material 22, wherein a portion of the piezoelectric material 22 arranged between the top side electrode 28 and the bottom side electrode 20 embodies the active region 30 of the BAW MEMS resonator structure. The top side electrode 28 and the piezoelectric material 22 are overlaid with a hermeticity layer 32, an interface layer 34, and a self-assembled monolayer (SAM) 36. Portions of the SAM 36 between the active region 30 and the walls 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte. Walls 44 that are laterally displaced from the active region 30 extend upward from the SAM 32 to define lateral boundaries of the microfluidic passage 52 containing the active region 30. The walls 44 may be formed of any suitable material, such as a laser-cut "stencil" layer of thin polymeric materials and/or laminate materials, optionally including one or more self-adhesive surfaces (e.g. adhesive tape). Optionally such walls 44 may be formed prior to deposition of the SAM 36, functionalization material 38, and chemical or biological blocking material 54 with an SU-8 negative epoxy resist or other photoresist material. The cover or cap layer 46 defining upper surface fluidic ports 48A, 48B is further provided to provide an upper boundary for the microfluidic passage 52. The cover or cap layer 46 may be formed by defining ports (e.g., via laser cutting or water jet cutting) in a layer of an appropriate material (e.g., a substantially inert polymer, glass, silicon, ceramic, or the like), and adhering the cover or cap layer 46 to top surfaces of the walls 44.

In use of the fluidic device 50, a fluid sample may be supplied through the first fluidic port 48A into the microfluidic passage 52 over the active region 30 and through the second fluidic port 48B to exit the microfluidic passage 52. Due to the laminar nature of the fluid flow within the microfluidic passage 52, the fluid volume may be modeled and behave as a "stack" of horizontal fluid layers including a lowermost fluid layer 40A and an uppermost fluid layer 40N. An analyte 42 contained in the lowermost fluid layer 40A of the fluid sample will tend to bind with functionalization material 38 arranged over the active region 30. Analyte contained in fluid layers above the lowermost fluid layer 40A (including the uppermost fluid layer 40N) may not be available to bind with the functionalization material 38, since diffusion of analyte (e.g., in a vertical direction) between the fluid layers 40A-40N may occur slowly. Assuming that sufficient analyte is present proximate to the lowermost fluid layer 40A to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude magnitude property, a frequency property, or a phase property, such as a shift in resonant frequency) of the BAW resonator structure may be detected to indicate a presence and/or quantity of analyte bound to the functionalization material 38.

To promote mixing of analyte within the fluid layers 40A-40N, the BAW resonator structure embodied in the fluidic device 50 of FIG. 4 may be driven at a frequency configured to cause the piezoelectric material 22 to exhibit a dominant longitudinal response. When it is desired to promote detection of analyte bound to the functionalization material 38, the BAW resonator structure embodied in the fluidic device 50 may be driven at a frequency configured to cause the piezoelectric material 22 to exhibit a dominant shear response.

In one example, a hexagonal crystal structure piezoelectric material comprising a c-axis having an orientation distribution that is predominantly non-parallel to normal of a face of a substrate (e.g., in a range of from 15 to 35 degrees) and having a thickness of 0.94 microns may exhibit a dominant shear response when driven at a frequency of about 2900 MHz, and may exhibit a dominant longitudinal response when driven at a frequency of about 5000 MHz. As will be recognized by one skilled in the art upon review of this disclosure, different piezoelectric material thicknesses and different driving frequencies may be used in certain embodiments.

Figure 5:
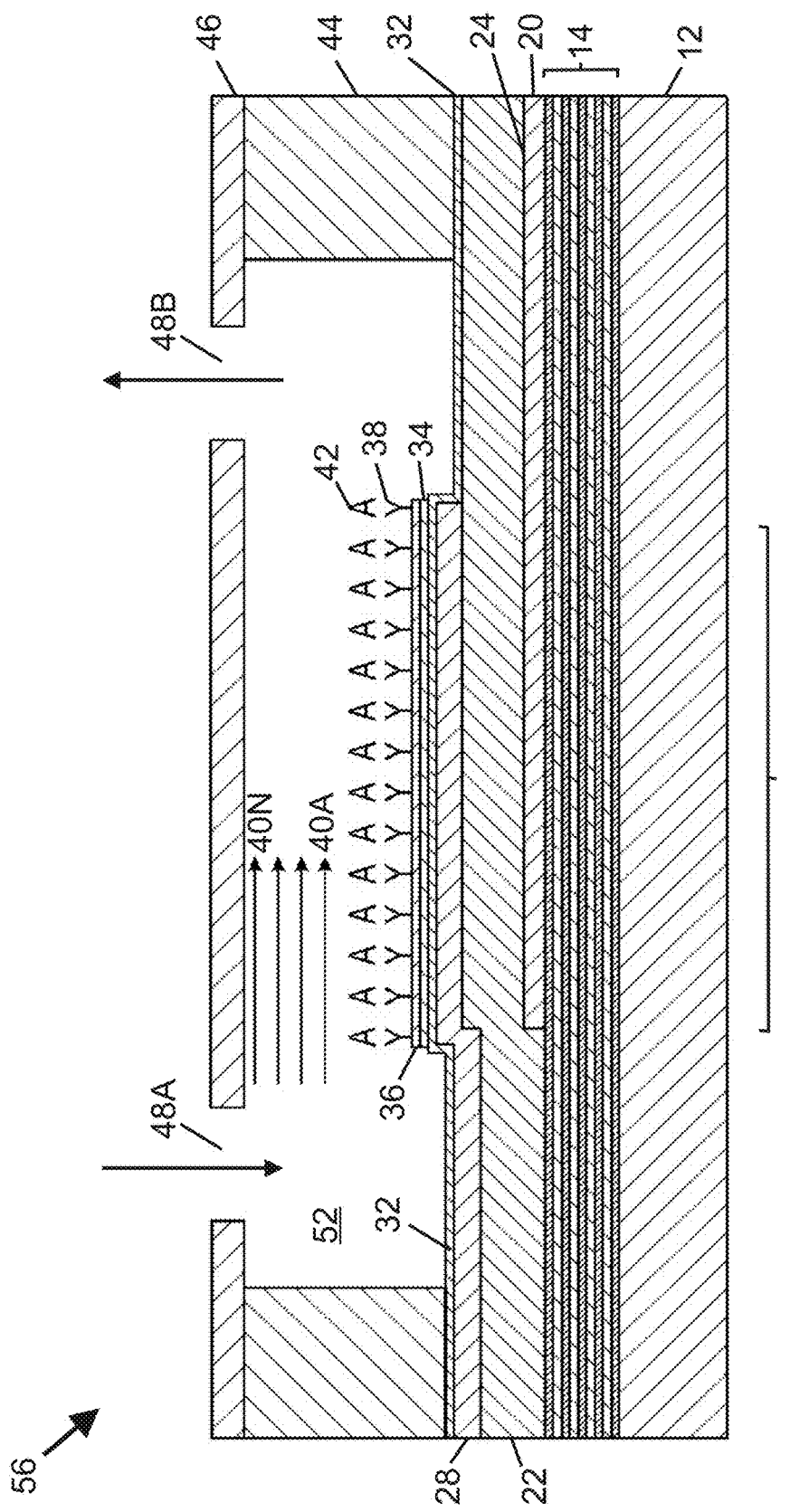
FIG. 5 is a schematic cross-sectional view of a portion of a fluidic device (e.g., a biochemical sensor device) including a microfluidic passage bounded from below by a BAW resonator structure, bounded laterally by walls, and bounded from above by a cover defining fluidic ports, with a hermeticity layer covering the BAW resonator structure, and with an interface layer, SAM, and functionalization material covering only the active region, according to one embodiment.

FIG. 5 is a schematic cross-sectional view of a portion of a fluidic device (e.g., a biochemical sensor device) 56 similar to the fluidic device 50 of FIG. 4, but including an interface layer 34 and a SAM 36 that are provided solely over an active region 30 instead of over an entirety of piezoelectric material 22. Such configuration may be provided by patterning of the interface layer 34. The fluidic device 56 includes a microfluidic passage 52 that is bounded from below by a bulk acoustic wave MEMS resonator structure including the active region 30, bounded laterally by walls 44, and bounded from above by a cover or cap layer 46 defining fluidic ports 48A, 48B. The fluidic device 56 includes a substrate 12 overlaid with an acoustic reflector 14, and a bottom side electrode 20 arranged generally below the piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW MEMS resonator structure. A hermeticity layer 32 is arranged over the top electrode 28 and the piezoelectric material 22. The interface layer 34 and the SAM 36 are provided over a portion of the hermeticity layer 32 registered with the active region 30. The SAM 36 is overlaid with a layer of functionalization (e.g., specific binding) material 38 arranged to bind at least one analyte (e.g., analyte 42). Walls 44 that are laterally displaced from the active region 30 extend upward from the hermeticity layer 32 to define lateral boundaries of the microfluidic passage 52 containing the active region 30. The cover or cap layer 46 defining upper surface fluidic ports 48A, 48B is provided over the walls 44 to provide an upper boundary for the microfluidic passage 52. Operation of the fluidic device 56 of FIG. 5 is similar to the operation of the fluidic device 50 of FIG. 4. A volume of fluid may behave as a "stack" of horizontal fluid layers including a lowermost fluid layer 40A and an uppermost fluid layer 40N within the fluidic passage 52, wherein the lowermost fluid layer 40A is proximate to functionalization material 38 overlying the active region 30.

Figure 6A:
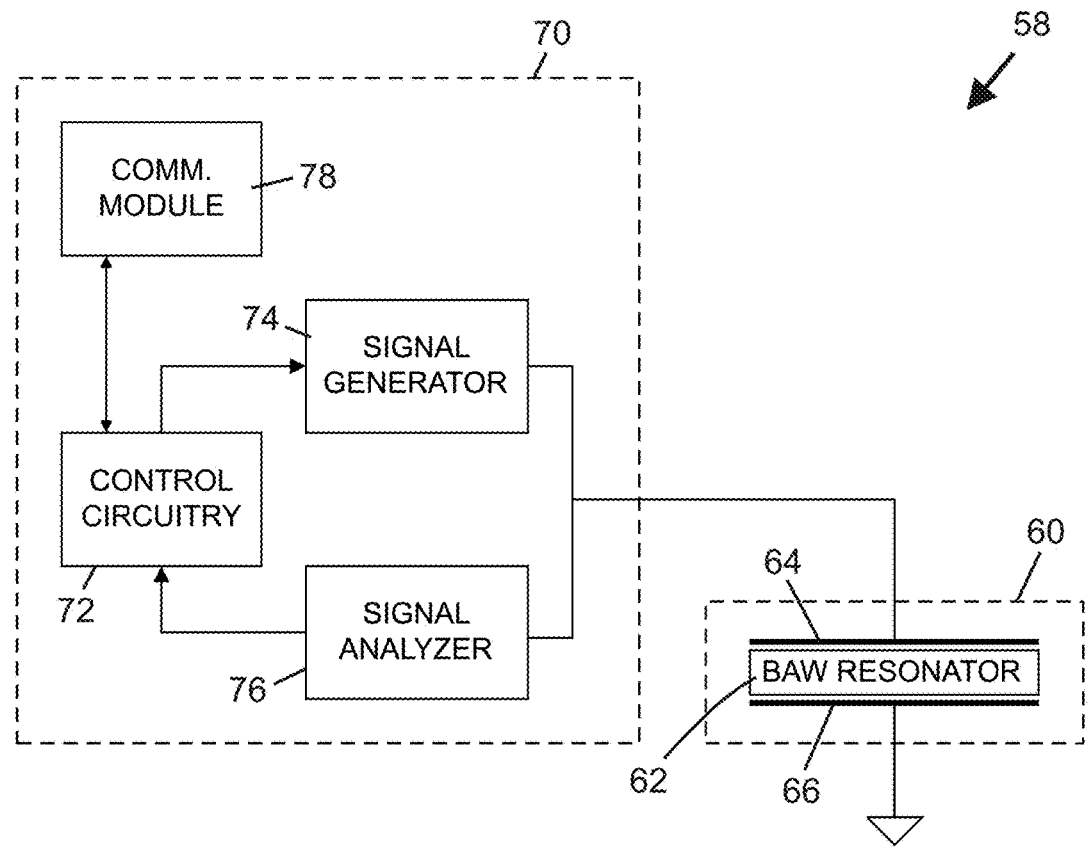
FIG. 6A is a schematic block diagram showing electrical components of a sensing system including a BAW resonator structure according to one embodiment.

FIG. 6A is a schematic block diagram showing electrical components of a sensing system 58 including a BAW resonator structure 62 according to one embodiment. The sensing system 58 includes a sensing portion 60 and a control portion 70. In certain embodiments, the sensing portion 60 may be embodied in a fluidic device configured as a cartridge that is suitable for use with an instrument that includes the control portion 70. In other embodiments, one or more components of the control portion 70 may be integrated with a fluidic device that includes the sensing portion 60. Within the sensing portion 60, the BAW resonator structure 62 includes top side and bottom side electrodes 64, 66, with at least one electrode 64, 66 being arranged in electrical communication with the control portion 70. The control portion 70 includes control circuitry 72 arranged to provide signals to a signal generator 74, and arranged to receive signals from a signal analyzer 76. The control circuitry 72 may also be coupled with a communication module 78.

The control circuitry 72 may include a central processing unit (CPU) and memory to enable the control circuitry 72 to directionally or bi-directionally communicate with the communication module 78 or other devices over a communication bus or another appropriate communication interface. The control circuitry 72 may communicate output information and/or receive instructions from the communication module 78. In certain embodiments, the signal analyzer 76 may include a digital signal processing module.

In certain embodiments, the control circuitry 72 may be used to control operation of the signal generator 74 to adjust at least one alternating current signal supplied to the BAW resonator structure 62. Such adjustment may include applying alternating current signals at different frequencies (optionally in conjunction with different magnitudes) to cause the BAW resonator structure 62 to selectively exhibit a dominant shear response (e.g., for analyte detection) or a dominant longitudinal response (for mixing). In certain embodiments, the BAW resonator structure 62 may be driven at a first frequency configured to cause the BAW resonator structure 62 to exhibit a dominant longitudinal response during a first time window, and may be driven at a second frequency configured to cause the BAW resonator structure 62 to exhibit a dominant shear response during a second time window. In certain embodiments, the second time window is non-overlapping with the first time window. In other embodiments, at least a portion of the second time window overlaps with the first time window. For example, in certain embodiments, alternating current signals of different frequencies may be applied simultaneously, to cause the BAW resonator structure 62 to exhibit both longitudinal and shear responses to promote fluid movement and mixing while detection is being performed.

In certain embodiments, an alternating current signal configured to cause the BAW resonator structure 62 to exhibit a dominant shear response may be controlled to provide a sweep of adjacent frequencies in order to detect a resonant frequency of the BAW resonator structure 62. Such resonant frequency may be altered based on adsorption of mass (e.g., analyte) to functionalization material associated with the BAW resonator structure 62. In this manner, performance of frequency sweeps prior to and after exposure of the BAW resonator structure 62 (including an active region overlaid with functionalization material) to analyte may be used to detect changes in resonant frequency indicative of presence and/or concentration of analyte bound to (e.g., adsorbed by) the functionalization material. As will be discussed in connection with FIGS. 7A and 7B, in certain embodiments, the control portion 70 may be used to implement a hill-climbing algorithm to locate a maximum amplitude at the resonant frequency of the BAW resonator structure 62.

With continued reference to FIG. 6A, the signal generator 74 preferably includes one or more oscillators arranged to output alternating current signals of different frequencies. In certain embodiments, the signal generator 74 may include a voltage controlled oscillator with a frequency dependent on an input voltage bias, providing an alternating current (e.g., square wave) output waveform with an output frequency that may be tuned with appropriate biasing resistors and capacitors.

In certain embodiments, the signal analyzer 76 is configured to receive one or more signals indicative of electroacoustic response of the BAW resonator structure 62 (such as voltage, current, frequency, and/or phase, to name a few). These signals may be received by the signal analyzer 76 while the BAW resonator structure 62 receives a signal from the signal generator 74 configured to cause the BAW resonator structure 62 to exhibit a dominant shear response.

Figure 6B:
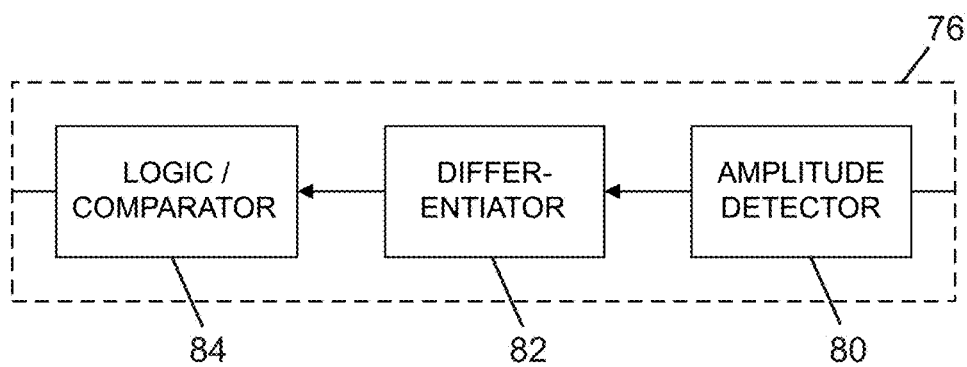
FIG. 6B is a schematic block diagram showing stages internal to a signal analyzer of the electrical components of a sensing system depicted in FIG. 6A.

FIG. 6B is a schematic block diagram showing stages internal to the signal analyzer 76 of the electrical components of the sensing system 58 depicted in FIG. 6A. In certain embodiments, the signal analyzer 76 may include an amplitude detector stage 80, a differentiator stage 82, and a logic (or comparator) stage 84. An exemplary amplitude detector stage 80 may include a high-pass filter, an amplifier, a precision full-wave rectifier, and a low-pass filter arranged in sequence. A high-pass filtered input signal received from the BAW resonator structure 62 may be amplified and then rectified, whereby the amplitude may be obtained by capturing the envelope of the rectified signal using the low-pass filter. The differentiator stage 82 may be composed of low-pass filters and a differentiator to determine the change in resonator signal with respect to time. A favorable and an unfavorable change in response may be defined as a positive and negative differentiation signal, respectively, and the low-pass filters may be used to reduce any high-frequency ripple resulting from envelope detection, thereby maintaining an acceptable signal-to-noise ratio. The logic (or comparator) stage 84 may determine the direction of sweep based on a change in response with respect to time, and may trigger a change in direction in a hill-climbing function when a differentiation signal changes from positive to negative. An exemplary logic stage 84 may include a comparator, a toggle flip flop, and an integrator. An output state of the comparator may be used to determine the direction of a driving frequency sweep. The integrator of the logic stage 84 may be used to integrate the digital signal of the comparator and generate an output signal of the signal analyzer 76 that may be provided to the control circuitry 72. Such signal may optionally be communicated by the control circuitry 72 to the signal generator 74 and/or the communication module 78 (shown in FIG. 6A).

With further reference to FIG. 6A, in certain embodiments, the control circuitry 72 in combination with the signal generator 74 may be considered a driving circuit configured to apply alternating current across the bottom side electrode 66 and the top side electrode 64 at a first frequency configured to cause piezoelectric material of the BAW resonator structure 62 to exhibit a dominant shear response, and configured to apply alternating current across the bottom side electrode 66 and the top side electrode 64 at a second frequency configured to cause the piezoelectric material to exhibit a dominant longitudinal response. Similarly, in certain embodiments, the signal analyzer 76, optionally in combination with the control circuitry 72, may be considered a detection circuit configured to detect a change in electroacoustic response of the BAW resonator structure 62 upon interaction of an analyte contained in fluid and at least one functionalization material. As will be recognized by one skilled in the art upon review of the present disclosure, other driving circuits and/or detection circuits may be used.

Figure 7A:
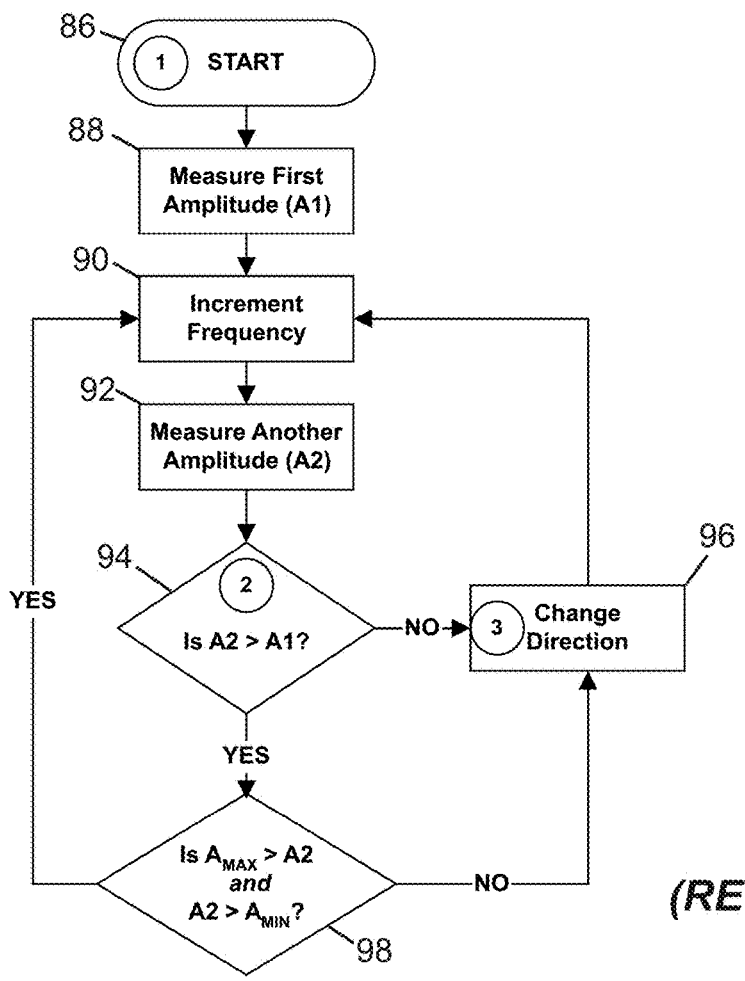
FIG. 7A is a flowchart outlining steps of a conventional voltage peak detection method useable with a sensing system according to certain embodiments.
Figure 7B:
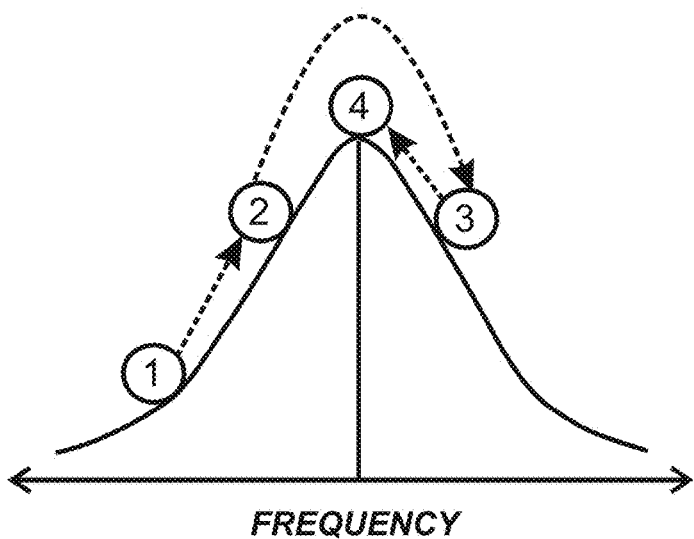
FIG. 7B is an exemplary plot of voltage amplitude versus frequency for a voltage peak, with identification of four events encountered in a conventional voltage peak detection method according to FIG. 7A.

FIG. 7A is a flowchart outlining steps of a conventional voltage peak detection method utilizing a hill-climbing algorithm, useable with a sensing system according to certain embodiments, and FIG. 7B is an exemplary plot of voltage amplitude versus frequency for a voltage peak, with identification of four events encountered in the conventional voltage peak detection method of FIG. 7A. FIGS. 7A and 7B are similar to figures provided in Xiao Zhu Fan et al., "An adaptive feedback circuit for MEMS resonators," *J. Micromech. Microeng.* 21 (2011) 045008. The hill-climbing algorithm sweeps actuation frequencies to locate the local maximum amplitude of a resonator system, through which the resonant frequency can be determined. Hill climbing locally sweeps the value of a function, and compares the present state to the past state until an extremum is located. If the present state is preferred over the past state, then the direction of the local sweep remains the same; conversely, if the past state is preferred, then the direction of the sweep reverses. Referring to FIG. 7A, an exemplary hill-climbing algorithm sweeps a range of actuation frequencies starting at a random point in a random direction according to block 86. Amplitude (A1) at one frequency is measured at block 88. The frequency is incremented at block 90, amplitude (A2) at another frequency is measured at block 92, and the current amplitude (A2) and the prior amplitude (A1) are compared at block 94. The algorithm will continue to sweep the frequency in the more favorable direction until a maximum response is achieved at the resonant frequency. The frequency sweep may change direction at block 96 if a reduced amplitude is detected. Once the resonant frequency is reached at block 98, a small steady-state oscillation will occur as the algorithm sweeps around the optimal point, changing directions as it passes the apex. The small steady-state oscillation around the resonant frequency is averaged (using a running average) to determine an estimate of the resonant frequency based on the assumption that the averaged time period is much smaller than the time required to shift the resonant frequency. Four events encountered in the conventional voltage peak detection method of FIG. 7A are identified in FIG. 7B, including a first event in which a starting frequency is selected, second and third events in which frequency is increased, and a fourth event in which a frequency corresponding to maximum amplitude (signifying a resonant frequency) is identified.

As noted previously, when a BAW resonator structure is driven at a frequency that causes piezoelectric material therein to exhibit a dominant longitudinal response, rotary mixing zones may be induced along at least one peripheral edge of a top side electrode. In such mixing zones, fluid and any analyte therein may be subjected to rotary motion. In certain embodiments, fluid and analyte may move along a toroidal or hollow circular path adjacent to a peripheral edge of the top side electrode to promote mixing. To increase mixing efficiency, in certain embodiments one or more recesses may be defined in upper portions of a top side electrode to form additional mixing zones. Driving of a BAW resonator structure at a frequency that causes piezoelectric material therein to exhibit a dominant longitudinal response induces localized rotational motion of the fluid proximate to one or more recesses. Such recesses may be formed by any suitable process, including photolithographic etching. In certain embodiments, one or more recesses are defined through less than the entire thickness of a top side electrode. In certain embodiments, the top side electrode comprises at least one lateral edge, and the one or more recesses include terminal ends non-coincident with at least one lateral edge.

Figure 8A:
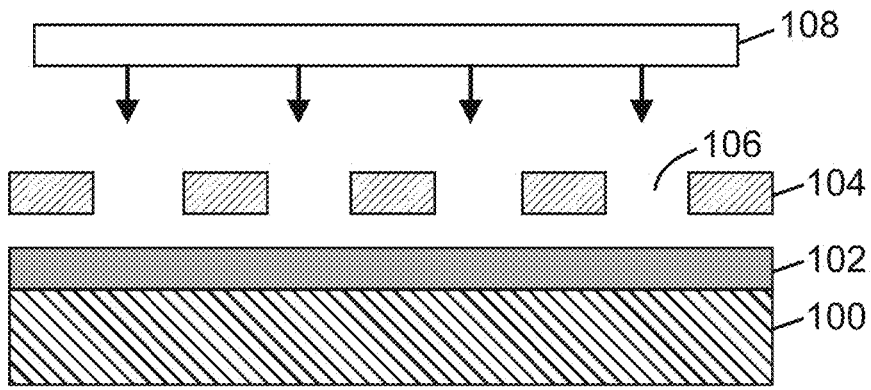
FIGS. 8A-8E provide schematic cross-sectional views of a portion of a top side electrode with recesses in various states of formation in an upper surface thereof.
Figure 8B:
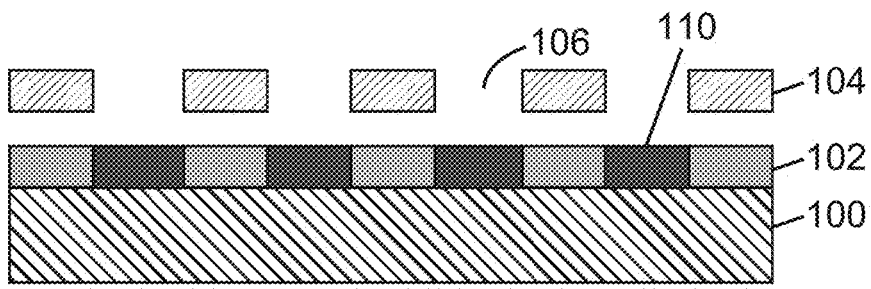
Figure 8C:
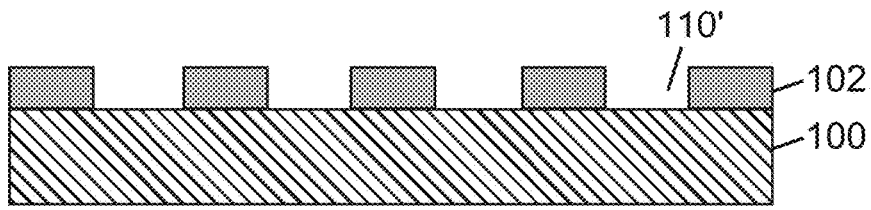
Figure 8D:
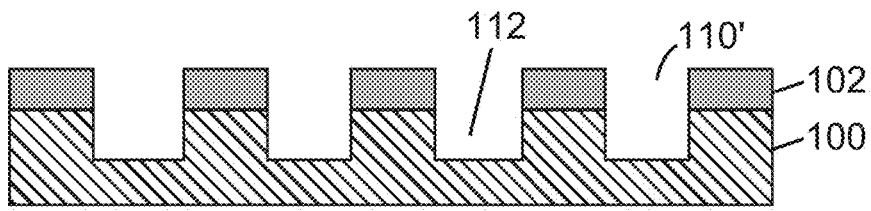
Figure 8E:
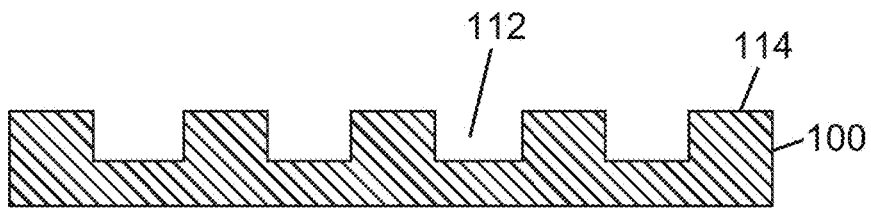

FIGS. 8A-8E provide schematic cross-sectional views of a portion of a top side electrode 100 with recesses in various states of formation in an upper surface thereof using a process such as photolithographic etching. FIG. 8A illustrates the top side electrode 100 overlaid with a layer of photoresist 102, with a photomask 104 defining mask windows 106 arranged between the layer of photoresist 102 and an electromagnetic (e.g., ultraviolet) radiation source 108. FIG. 8B illustrates the photomask 104, top side electrode 100, and layer of photororesist 102 following impingement of radiation through the mask windows 106 to form soluble regions 110 in the layer of photoresist 102. Such soluble regions 110 may be removed by application of a suitable developer chemical to yield a layer of photoresist 102 defining photoresist windows 110', as shown in FIG. 8C. Thereafter, a suitable etchant may be applied to through the photoresist windows 110' to form grooves or recesses 112 in the top side electrode 100, as shown in FIG. 8D. Finally, the layer of photoresist 102 may be removed to yield a top side electrode 100 including an exposed upper surface 114 and grooves or recesses 112 that extend from the upper surface 114 into an interior of the top side electrode 100, as shown in FIG. 8E. The resulting grooves or recesses 112 may be used to promote fluid movement and mixing by inducing rotary movement of liquid proximate to the grooves or recesses 112 upon application of an alternating current signal configured to cause an associated BAW resonator structure to exhibit a dominant longitudinal response. Although FIG. 8E shows the grooves or recesses 112 as extending through only a portion of a thickness of the top side electrode 100, in certain embodiments, one or more grooves or recesses 112 may extend through the entire thickness of the top side electrode 100, provided that the one or more grooves or recesses 112 would be configured so as not to interrupt electrical connection to the remainder of the top side electrode 100.

Figure 9A:
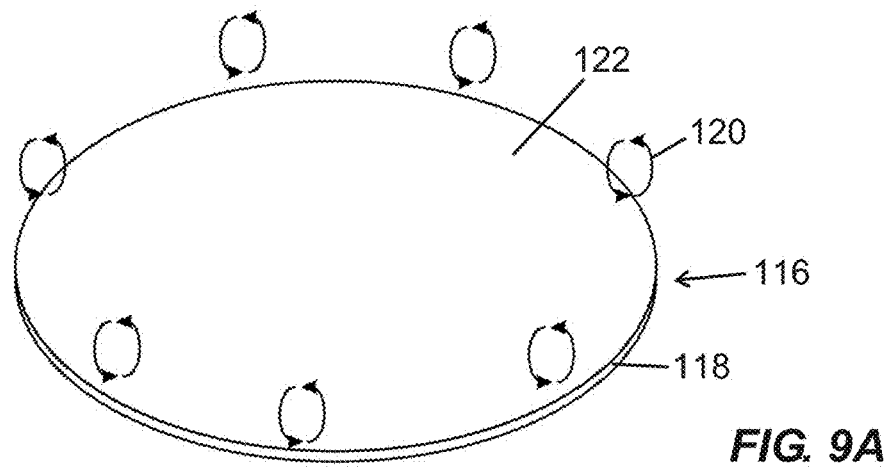
FIG. 9A is a schematic perspective view of a top side electrode having a round configuration and being devoid of recesses, showing inducement of rotary mixing zones along a peripheral edge of the top side electrode upon application of an alternating current signal configured to cause a BAW resonator structure incorporating the top side electrode to exhibit a dominant longitudinal response.

FIG. 9A is a schematic perspective view of a top side electrode 116 of a BAW resonator structure as disclosed herein, with the top side electrode 116 having a round configuration with a peripheral edge 118 but without any recesses defined in a top surface 122 thereof. Upon application of an alternating current signal configured to cause a BAW resonator structure incorporating the top side electrode 116 to exhibit a dominant longitudinal response, rotary mixing zones 120 are induced along the peripheral edge 118 of the top side electrode 116. The rotary mixing zones 120 cause fluid proximate to the top side electrode 116 to move along a toroidal or hollow circular path adjacent to the peripheral edge 118, and such motion may enhance mixing, thereby increasing the rate of binding of analyte contained in the fluid to functionalization material associated with the top side electrode 116.

Figure 9B:
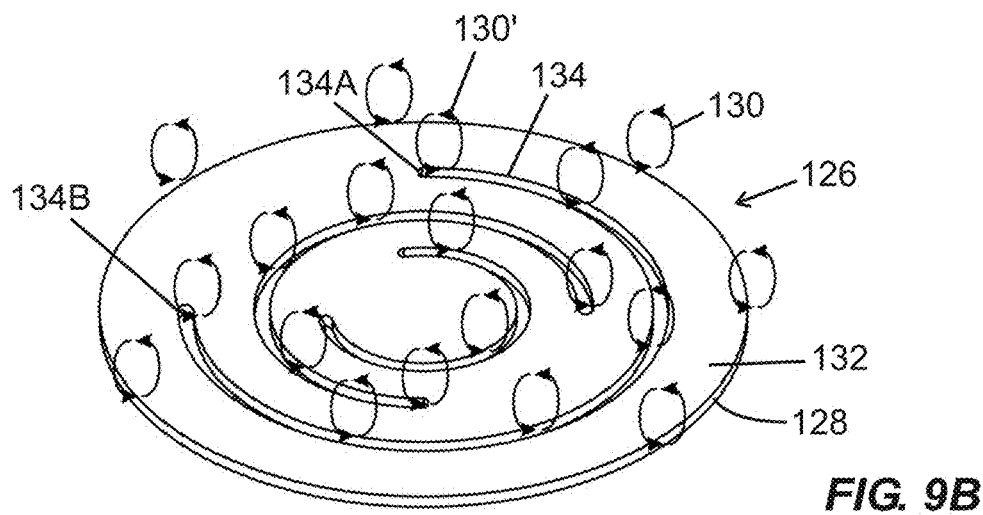
FIG. 9B is a schematic perspective view of a top side electrode having a round shape and including concentric, major arc-shaped recesses defined therein, showing inducement of rotary mixing zones along a peripheral edge and along the recesses upon application of an alternating current signal configured to cause a BAW resonator structure incorporating the top side electrode to exhibit a dominant longitudinal response.

FIG. 9B is a schematic perspective view of a top side electrode 126 of a BAW resonator structure as disclosed herein, with the top side electrode 126 having a round shape configuration with a peripheral edge 128 and including concentric, major arc-shaped recesses 134 defined in an upper surface 132 thereof. Each recess 134 includes terminal ends 134A, 134B that are non-coincident with the peripheral edge 128, each recess 134 is substantially concentric along the upper surface 132, and each recess 134 is laterally displaced and non-intersecting relative to each other recess 134. Upon application of an alternating current signal configured to cause a BAW resonator structure incorporating the top side electrode 126 to exhibit a dominant longitudinal response, rotary mixing zones 130 are induced along the peripheral edge 128 of the top side electrode 126, and additional rotary mixing zones 130' are induced along the recesses 134. Relative to a top side electrode lacking recesses (such as shown in FIG. 9A), presence of the recesses 134 along the upper surface 132 of the top side electrode 126 of FIG. 9B promotes additional fluid movement and enhanced mixing of fluid adjacent to a greater portion of the upper surface 132 of the top side electrode 126 (i.e., not just proximate to the peripheral edge 128). In certain embodiments, each recess 134 does not extend through the entire thickness of the top side electrode 126. In other embodiments, one or more recesses 134 may extend through an entire thickness of the top side electrode 126, but as shown in FIG. 9B, the recesses 134 are arranged in such a manner as to prevent electrical disconnection of any portions of the top side electrode 126, such that electrical communication to the entre top side electrode 126 is maintained.

Figure 9C:
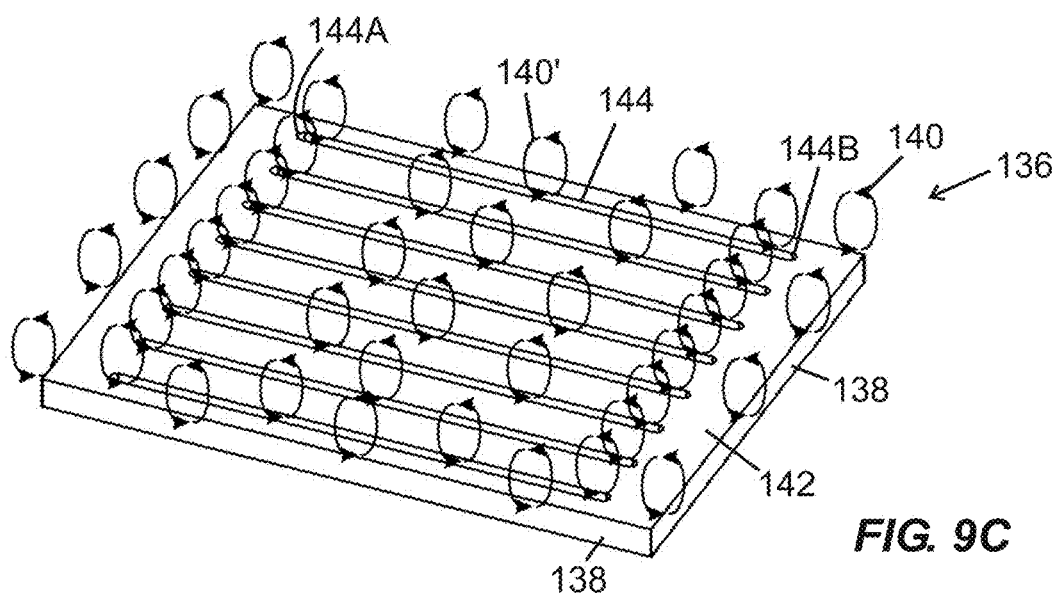
FIG. 9C is a schematic perspective view of a top side electrode having a rectangular configuration and including parallel linear recesses defined therein, showing inducement of rotary mixing zones along a peripheral edge and along the recesses upon application of an alternating current signal configured to cause a BAW resonator structure incorporating the top side electrode to exhibit a dominant longitudinal response.

FIG. 9C is a schematic perspective view of a top side electrode 136 having a rectangular configuration and including parallel linear recesses 144 defined in an upper surface 142 thereof. Each recess 144 includes terminal ends 144A, 144B that are non-coincident with peripheral edges 138 of the top side electrode 136, and each recess 144 is laterally displaced and non-intersecting relative to each other recess 144. Upon application of an alternating current signal configured to cause a BAW resonator structure incorporating the top side electrode 136 to exhibit a dominant longitudinal response, rotary mixing zones 140 are induced along peripheral edges 138 of the top side electrode 136, and additional rotary mixing zones 140' are induced along the recesses 144.

Although top side electrodes 116, 126 having round shapes are shown in FIGS. 9A and 9B, and a top side electrode 136 having a rectangular shape is shown in FIG. 9C, it is to be recognized that top side electrodes of other shapes and including recesses in configurations other the specific configurations shown in FIGS. 9A-9C may be provided in other embodiments.

Experiments were conducted to evaluate the effect of radio frequency (RF) power applied to electrodes of a microfluidic sensor device incorporating a BAW resonator structure with a piezoelectric material having a c-axis orientation distribution non-perpendicular relative to a face of an underlying substrate. An alternating current signal having a frequency configured to cause the piezoelectric material to exhibit a dominant longitudinal response was used to induce fluid flow and mixing. In the experiment, 1 micron diameter melamine beads in an aqueous solution were introduced into a channel of the microfluidic sensor device in order to observe fluid flow.

Figure 10A:
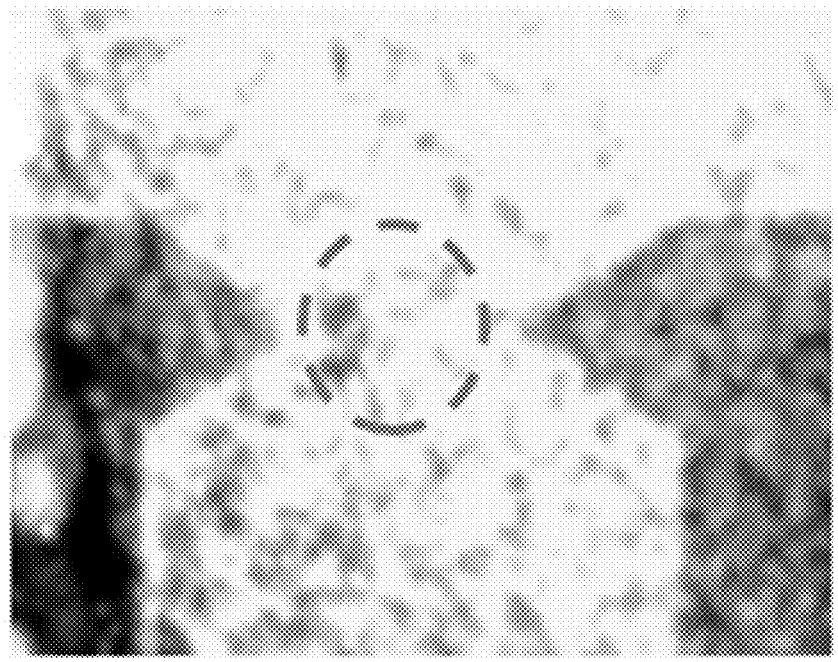
FIG. 10A is a top plan view digital photograph of a portion of a fluidic device including a BAW resonator structure with a circular shaped top side electrode of an active region (corresponding to a dashed line circle superimposed over the photograph), with the fluidic device containing a liquid with melamine beads, and the melamine beads flowing in a laminar fashion with the fluid flow over the active region.
Figure 10B:
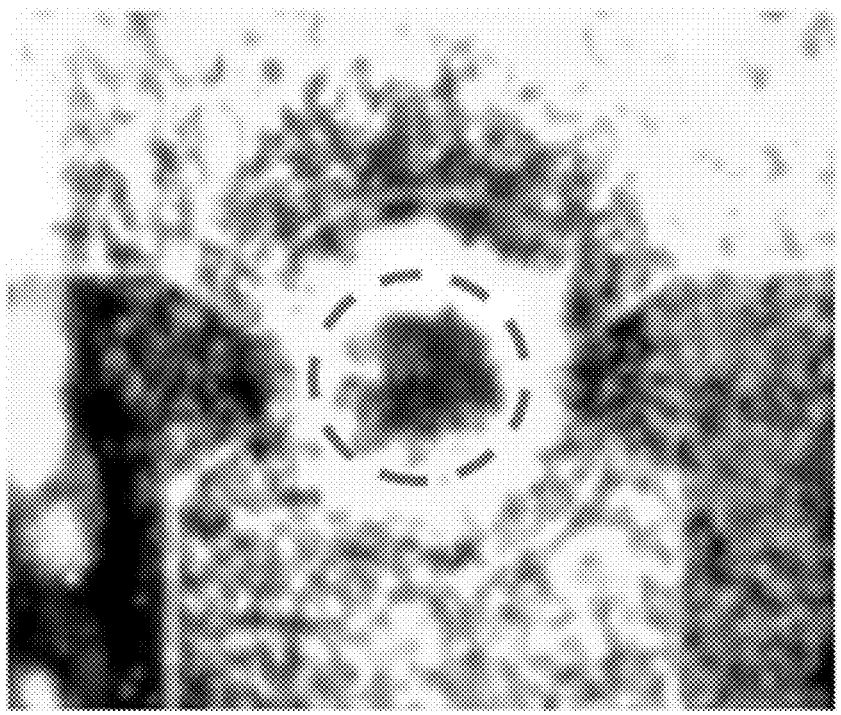
FIG. 10B is top plan view digital photograph of the portion of a fluidic device according to FIG. 10A, with the BAW resonator structure being driven with an alternating current signal at a frequency causing piezoelectric material in the active region to exhibit a dominant longitudinal response, thereby causing fluid and melamine beads proximate to the active region to move along a toroidal or hollow circular path adjacent to a peripheral edge of the circular shaped top side electrode to promote mixing in a circular pattern.

FIGS. 10A and 10B are top plan view digital photographs showing states in which RF power inducing a dominant longitudinal response was not applied and was applied, respectively, wherein each image includes a superimposed dotted line circle corresponding to an edge of a top side electrode corresponding to an active region. As shown in FIG. 10A, when no RF power inducing a dominant longitudinal response was applied, the melamine beads (embodying a white or light colored region) moved coincident with the fluid flow in a laminar manner past the active region. Conversely, as shown in FIG. 10B, when RF power inducing a dominant longitudinal response was applied, the melamine beads moved in a toroidal or hollow circular manner adjacent to a peripheral edge of the top side electrode corresponding to the active region. In FIG. 10B, the bright white zone near the peripheral edge of the top side electrode corresponds to a high concentration of melamine beads moving in a toroidal or hollow circular pattern.

FIG. 11A is a schematic cross-sectional view of a film bulk acoustic wave resonator (FBAR) structure 150 including an active region 30, wherein at least portions of the active region 30 are subject to being overlaid with an interface layer and a self-assembled monolayer (SAM) suitable for receiving a functionalization (e.g., specific binding or non-specific binding) material, according to one embodiment. The FBAR structure 150 includes a substrate 152 (e.g., silicon or another semiconductor material) defining a cavity 154 optionally covered by a support layer 156 (e.g., silicon dioxide). A bottom side electrode 20 is arranged over a portion of the support layer 156, a piezoelectric material 22, preferably embodying inclined c-axis hexagonal crystal structure piezoelectric material (e.g., AlN or ZnO), is arranged over the bottom side electrode 20 and the support layer 156, and a top side electrode 28 is arranged over at least a portion of a top surface of the piezoelectric material 22. A portion of the piezoelectric material 22 arranged between the top side electrode 28 and the bottom side electrode 20 embodies the active region 30 of the FBAR structure 150. The active region 30 is arranged over and registered with the cavity 154 disposed below the support layer 156. The cavity 154 serves to confine acoustic waves induced in the active region 30 by preventing dissipation of acoustic energy into the substrate 152, since acoustic waves do not efficiently propagate across the cavity 154. In this respect, the cavity 154 provides an alternative to the acoustic reflector 14 illustrated in FIGS. 2, 4, and 5. Although the cavity 154 shown in FIG. 11A is bounded from below by a thinned portion of the substrate 152, in alternative embodiments at least a portion of the cavity 154 may extend through an entire thickness of the substrate 152. Steps for forming the FBAR structure 150 may include defining the cavity 154 in the substrate 152, filling the cavity 154 with a sacrificial material (not shown) optionally followed by planarization of the sacrificial material, depositing the support layer 156 over the substrate 152 and the sacrificial material, removing the sacrificial material (e.g., by flowing an etchant through vertical openings defined in the substrate 152 or the support layer 156, or lateral edges of the substrate 152), depositing the bottom side electrode 20 over the support layer 156, growing (e.g., via sputtering or other appropriate methods) the piezoelectric material 22, and depositing the top side electrode 28. In certain embodiments, the top side electrode 28, piezoelectric material 22, and the bottom side electrode 20 in combination may be self-supporting, and the support layer 76 may be omitted and/or removed by etching in the vicinity of the active area 30.

FIG. 11B is a schematic cross-sectional view of a FBAR structure 150 according to FIG. 11A, following addition of a hermeticity layer 32, an interface layer 34, a self-assembled monolayer 36, and functionalization material 38 (e.g., specific binding material). The hermeticity layer 32 is arranged over the entire piezoelectric material 22 (as well as the top side electrode 28), whereas the functionalization material 38, the SAM 36, and the interface layer 34 are arranged solely over the active region 30. As shown in FIG. 11B, analyte 42 is bound to the functionalization material 38, such as may occur following exposure of the functionalization material 38 to a medium (e.g., liquid or other fluid) containing the analyte 42, optionally as part of a microfluidic device.

As will be recognized by one skilled in the art upon review of the present disclosure, in certain embodiments the FBAR structure 150 of FIGS. 11A and 11B may be substituted for the solidly mounted BAW structures disclosed in FIGS. 4 and 5, and/or recesses may optionally be defined in the top side electrode 28 of the FBAR structure 150. In certain embodiments, the FBAR structure 150 of FIG. 11B may be incorporated in a fluidic device (e.g., microfluidic device) and/or a sensing system in which a driving circuit is configured to apply alternating current at different frequencies to cause the piezoelectric material 22 to selectively exhibit a dominant shear response or a dominant longitudinal response.

Figure 12:
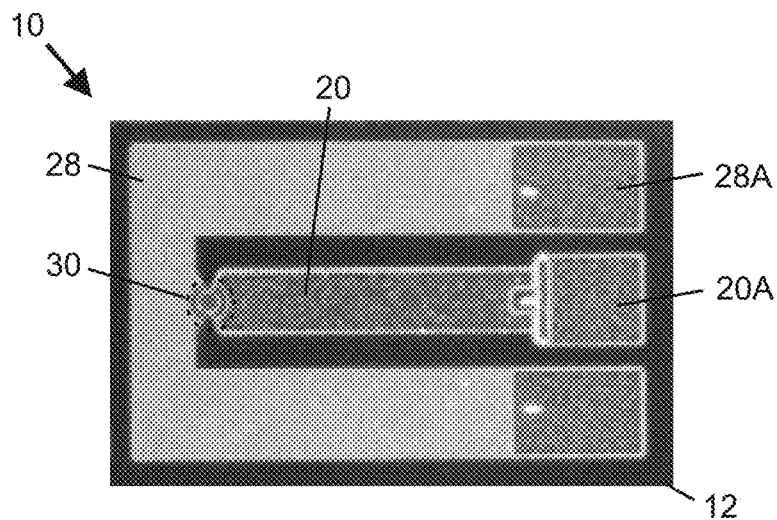
FIG. 12 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 12 is a top plan view photograph of a bulk acoustic wave MEMS resonator device 10 (consistent with the portion of the resonator device 10 illustrated in FIG. 2) suitable for receiving a hermeticity layer, an interface layer, a self-assembled monolayer, and/or functionalization (e.g., specific binding) material as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After portions of the resonator device 10 are overlaid with an interface layer, a self-assembled monolayer, and functionalization (e.g., specific binding) material as disclosed herein, the resonator device 10 may be used as a sensor and/or incorporated into a microfluidic device. If desired, multiple resonator devices 10 may be provided in an array on a single substrate 12.

Figure 13:
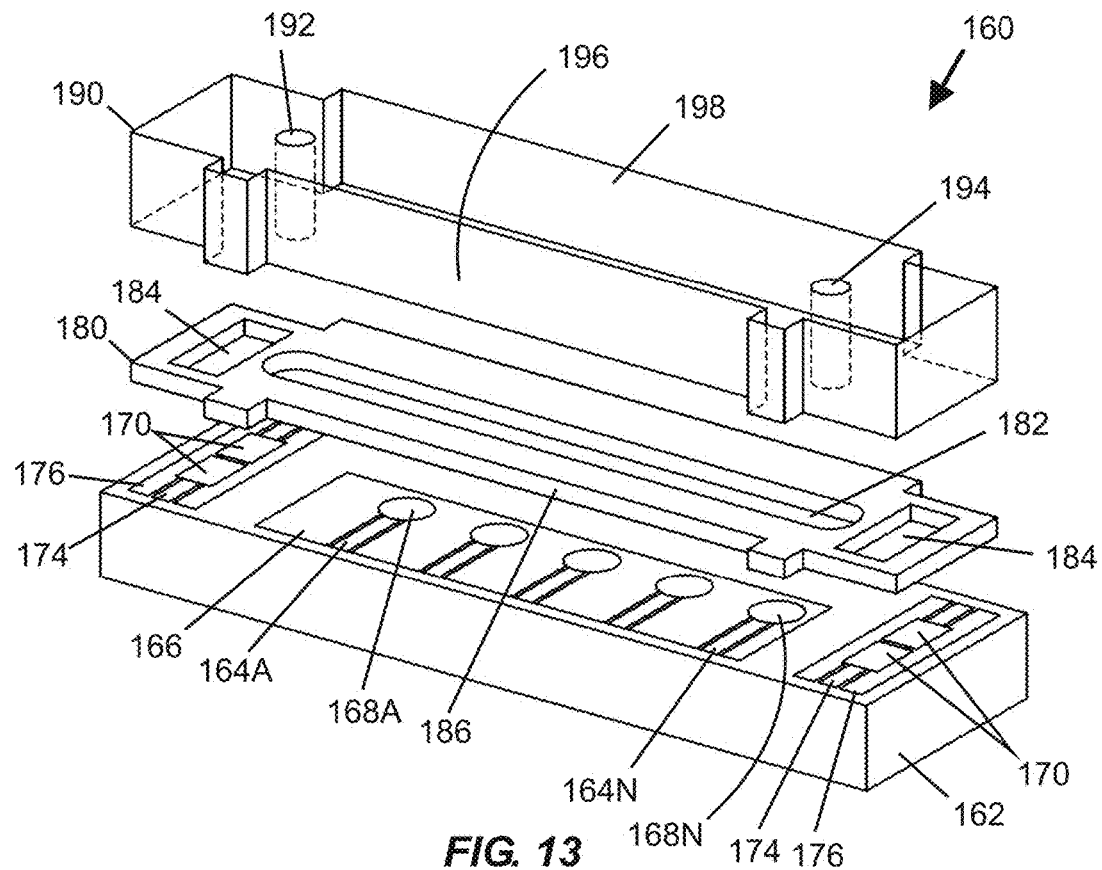
FIG. 13 is a perspective assembly view of a microfluidic device incorporating a substrate with multiple bulk acoustic wave MEMS resonator devices as disclosed herein, an intermediate layer defining a channel containing active regions of the MEMS resonator devices, and a cover or cap layer.

FIG. 13 is a perspective assembly view of a microfluidic device 160 incorporating a substrate 162 with multiple bulk acoustic wave MEMS resonator devices, an intermediate layer 180 defining a central microfluidic channel 182 registered with active regions 168A-168N of the MEMS resonator devices, and a cover or cap layer 190 arranged to cover the intermediate layer 180. Top central portions of the substrate 162, which includes an acoustic reflector (not shown) and a piezoelectric material (not shown), include a top side electrode 166 and bottom side electrodes 164A-164N. Regions in which the foregoing electrodes overlap one another and sandwich the piezoelectric material embody active regions 168A-168N. Any suitable number of active regions 168A-168N may be provided and fluidically arranged in series or parallel, although five active regions are illustrated in FIG. 13. Top peripheral (or top end) portions of the substrate 162 further include reference top side electrodes 176 and reference bottom side electrodes 174 in communication with reference overlap regions 170. Such reference overlap regions 170 are not exposed to fluid, and are present to provide a basis for comparing signals obtained from the active regions 168A-168N exposed to fluid within the central microfluidic channel 182. The substrate 162 is overlaid with the intermediate (e.g., wall-defining) layer 180, wherein the central microfluidic channel 182 is intended to receive fluid, and defines peripheral chambers 184 arranged to overlie the reference overlap regions 170 in a sealed fashion. The intermediate layer 180 may be formed of any suitable material such as SU-8 negative epoxy resist, other photoresist material, or laser-cut "stencil" layers of thin polymeric materials optionally including one or more self-adhesive surfaces (e.g., adhesive tape), etc. The intermediate layer 180 further includes a lateral inset region 186 that enables lateral portions of the top side electrode 166 and bottom side electrodes 164A-164N to be accessed upon assembly of the microfluidic device 160. The cover or cap layer 190 includes a lateral inset region 196 registered with the lateral inset region 186 of the intermediate layer 180, and includes microfluidic ports 192, 194 accessible along a top surface 198 of the cover or cap layer 190 and registered with end portions of the central microfluidic channel 182 defined in the intermediate layer 180 to permit fluid (e.g., liquid) to be supplied to the central microfluidic channel 182 over the active regions 168A-168N. Preferably, at least the electrodes 164A-164N, 166 are overlaid with a hermeticity layer, an interface layer, a self-assembled monolayer, and functionalization (e.g., specific binding) material as disclosed herein.

In certain embodiments, one or more driving circuits may be configured to apply alternating current at different frequencies to the electrodes 164A-164N, 166 to cause the piezoelectric material to selectively exhibit a dominant shear response or a dominant longitudinal response. Additionally, in certain embodiments, recesses may optionally be defined in the top side electrode 166 of the microfluidic device 160. Microfluidic devices according to other configurations may be provided, as will be recognized by those skilled in the art upon review of the present disclosure.

In certain embodiments, a fluidic device incorporating a bulk acoustic wave resonator structure (e.g., a BAW resonator structure) with a piezoelectric material comprising a c-axis having an orientation distribution that is predominantly non-parallel to normal of a face of a substrate, and incorporating one or more layers (including functionalization material) overlying an active region, may be utilized in performance of various method steps. A pre-measurement step may include driving the bulk acoustic wave resonator structure with an alternating current signal at a first frequency configured to cause the piezoelectric material to exhibit a dominant shear response, to establish a baseline mass loading of the bulk acoustic wave resonator structure with "unpopulated" functionalization material, and similarly driving any associated reference sensor(s). The functionalization material may include specific binding material, or may include non-specific binding material. A subsequent (mixing and binding) step may include driving the bulk acoustic wave resonator structure with an alternating current signal at a second (e.g., higher) frequency configured to cause the piezoelectric material to exhibit a dominant longitudinal response, sufficient to promote localized fluid motion proximate to a top side electrode of the bulk acoustic wave resonator structure. At the same time, a fluid (e.g., liquid) containing analyte is flowed through a passage (e.g., channel) of the fluidic device to contact the functionalization material, whereby analyte within the fluid may be bound to the functionalization material. A subsequent detection step may include driving the bulk acoustic wave resonator structure with an alternating signal at a frequency (optionally equal to the first frequency) configured to cause the piezoelectric material to exhibit a dominant shear response, in order to determine mass loading of the bulk acoustic wave resonator structure for "populated" functionalization material (due to binding of analyte to functionalization material) overlying the active region. A further (analyte mass binding determination) step may include computing the mass of analyte bound to the functionalization material by comparing one or more signals obtained during the pre-measurement step with one or more signals obtained during the detection step. Optionally, comparison may also be made to a reference sensor to accommodate any baseline shift.

Technical benefits obtainable with various embodiments of the present disclosure may include one or more of the following: enhanced rate of analyte binding to functionalization material overlying an active region of a bulk acoustic wave resonator structure thereby reducing the time required to complete measurement of a particular sample; reduced footprint and/or cost of a sensing device providing both mixing and sensing utility since both functions may be performed with a single bulk acoustic wave resonator structure; and/or enhanced lower detection limit of a resonator-based liquid sensor.

Those skilled in the art will recognize improvements and modifications to the preferred embodiments of the present disclosure. All such improvements and modifications are considered within the scope of the concepts disclosed herein and the claims that follow.

What is claimed is:

1. A sensing system comprising:
a channel arranged to receive a fluid;
a bulk acoustic wave resonator structure arranged between a substrate and a surface bounding at least a portion of the channel, wherein the bulk acoustic wave resonator structure includes (i) a piezoelectric material comprising a c-axis having an orientation distribution that is predominantly non-parallel to normal of a face of the substrate, (ii) a bottom side electrode arranged between the piezoelectric material and the substrate, and (iii) a top side electrode arranged between the piezoelectric material and the channel, wherein at least a portion of the piezoelectric material is arranged between the bottom side electrode and the top side electrode to form an active region;
at least one functionalization material arranged over at least a portion of the top side electrode, wherein the at least one functionalization material is arranged to contact the fluid received by the channel; and
a driving circuit configured to apply alternating current across the bottom side electrode and the top side electrode at a first frequency and a second frequency to cause the piezoelectric material to exhibit a dominant shear response at the first frequency and a dominant longitudinal response at the second frequency.

2. The sensing system of claim 1, further comprising a detection circuit configured to detect a change in electroacoustic response of the bulk acoustic wave resonator structure upon interaction of an analyte contained in the fluid with the at least one functionalization material.

3. The sensing system of claim 1, wherein the top side electrode comprises at least one recess that is defined in a surface of the top side electrode proximate to the channel.

4. The sensing system of claim 3, wherein the top side electrode comprises at least one lateral edge, and the at least one recess includes terminal ends non-coincident with the at least one lateral edge.

5. The sensing system of claim 3, wherein the at least one recess comprises a first recess and a second recess, wherein the second recess is laterally displaced and non-intersecting relative to the first recess.

6. The sensing system of claim 1, wherein the at least one functionalization material comprises at least one of a specific binding material or a non-specific binding material.

7. The sensing system of claim 1, further comprising a self-assembled monolayer arranged between the top side electrode and the at least one functionalization material.

8. The sensing system of claim 1, further comprising an interface layer arranged between the top side electrode and the at least one functionalization material.

9. The sensing system of claim 8, wherein the top side electrode comprises a non-noble metal, and the bulk acoustic wave resonator structure further comprises a hermeticity layer arranged between the interface layer and the top side electrode.

10. The sensing system of claim 8, further comprising a self-assembled monolayer arranged between the interface layer and the at least one functionalization material.

11. The sensing system of claim 1, further comprising at least one acoustic reflector element arranged between the substrate and the bulk acoustic wave resonator structure.

12. The sensing system of claim 1, wherein the substrate defines a recess, and the active region is arranged over at least a portion of the recess.

13. A method for biological or chemical sensing, the method comprising:
supplying a fluid containing an analyte into a channel of the sensing system according to claim 1, wherein said supplying is configured to cause at least some of the analyte to bind to the at least one functionalization material;
inducing a bulk acoustic wave in the active region; and
detecting a change in electroacoustic response in at least one of a frequency property or a phase property of the bulk acoustic wave resonator structure upon binding of analyte to the at least one functionalization material.

14. A sensing method comprising:
supplying a fluid containing an analyte to a channel arranged proximate to a bulk acoustic wave resonator structure comprising a piezoelectric material including a c-axis having an orientation distribution that is predominantly non-parallel to normal of a face of a substrate, wherein at least a portion of the piezoelectric material is arranged between a top side electrode and a bottom side electrode to form an active region, at least one functionalization material is arranged over at least a portion of the active region, and the at least one functionalization material is arranged to contact the fluid supplied to the channel;
driving the bulk acoustic wave resonator structure at a first frequency configured to cause the piezoelectric material to exhibit a dominant longitudinal response to increase a rate of binding of analyte in the fluid to the at least one functionalization material;
driving the bulk acoustic wave resonator structure at a second frequency configured to cause the piezoelectric material to exhibit a dominant shear response; and
while driving the bulk acoustic wave resonator structure at the second frequency, detecting a change in electroacoustic response of the at least one bulk acoustic wave resonator structure caused by binding of analyte to the at least one functionalization material.

15. The sensing method of claim 14, wherein said driving of the bulk acoustic wave resonator structure at the first frequency is performed during a first time window, and said driving of the bulk acoustic wave resonator structure at the second frequency is performed during a second time window, wherein the second time window is non-overlapping with the first time window.

16. The sensing method of claim 14, wherein said driving of the bulk acoustic wave resonator structure at the first frequency is performed during a first time window, and said driving of the bulk acoustic wave resonator structure at the second frequency is performed during a second time window, wherein at least a portion of the second time window overlaps the first time window.

17. The sensing method of claim 14, wherein the top side electrode comprises at least one recess that is defined in a surface of the top side electrode proximate to the channel, and said driving of the bulk acoustic wave resonator structure at the first frequency is configured to induce localized rotational motion of the fluid proximate to the at least one recess.

18. A fluidic device comprising:
a channel arranged to receive a fluid;
a bulk acoustic wave resonator structure arranged between a substrate and a surface bounding at least a portion of the channel, wherein the bulk acoustic wave resonator structure includes (i) a piezoelectric material comprising a c-axis having an orientation distribution that is predominantly non-parallel to normal of a face of the substrate, (ii) a bottom side electrode arranged between the piezoelectric material and the substrate, and (iii) a top side electrode arranged between the piezoelectric material and the channel, wherein at least a portion of the piezoelectric material is arranged between the bottom side electrode and the top side electrode to form an active region; and
a driving circuit configured to apply alternating current across the bottom side electrode and the top side electrode at a first frequency and a second frequency to cause the piezoelectric material to exhibit a dominant shear response at the first frequency and a dominant longitudinal response at the second frequency;
wherein the top side electrode comprises at least one recess that is defined in a surface of the top side electrode proximate to the channel.

19. The fluidic device of claim 18, further comprising at least one functionalization material arranged over at least a portion of the top side electrode, wherein the at least one functionalization material is arranged to contact the fluid received by the channel.

20. The fluidic device of claim 18, wherein the at least one recess comprises a first recess and a second recess, wherein the second recess is laterally displaced and non-intersecting relative to the first recess.

* * * * *